(12) United States Patent
Hammack et al.

(10) Patent No.: US 12,090,088 B2
(45) Date of Patent: Sep. 17, 2024

(54) DEVICE FOR OCULAR ACCESS

(71) Applicant: CLEARSIDE BIOMEDICAL, INC., Alpharetta, GA (US)

(72) Inventors: Amy Lee Hammack, Santa Clara, CA (US); Stanley R. Conston, San Carlos, CA (US); Ronald Yamamoto, San Francisco, CA (US)

(73) Assignee: Clearside Biomedical, Inc., Alpharetta, GA (US)

( * ) Notice: Subject to any disclaimer, the term of this patent is extended or adjusted under 35 U.S.C. 154(b) by 0 days.

(21) Appl. No.: 17/523,168

(22) Filed: Nov. 10, 2021

(65) Prior Publication Data

US 2022/0062041 A1    Mar. 3, 2022

Related U.S. Application Data

(63) Continuation of application No. 17/208,235, filed on Mar. 22, 2021, now abandoned, which is a
(Continued)

(51) Int. Cl.
*A61F 9/00*      (2006.01)
*A61F 9/007*    (2006.01)
(Continued)

(52) U.S. Cl.
CPC ........ *A61F 9/0017* (2013.01); *A61F 9/00727* (2013.01); *A61F 9/00736* (2013.01);
(Continued)

(58) Field of Classification Search
CPC ................ A61M 5/46; A61M 25/0108; A61M 25/0643; A61M 25/065;
(Continued)

(56) References Cited

U.S. PATENT DOCUMENTS 1,527,291 A *   2/1925   Zorraquin ............... A61M 5/32
                                                          604/158
2,187,259 A       1/1940   Barnhart
(Continued)

FOREIGN PATENT DOCUMENTS

CA       2639322 A1    3/2009
CN       1229679 A     9/1999
(Continued)

OTHER PUBLICATIONS

Abbott Laboratories Inc., Abbott Park, Illinois, USA, Abbott Medical Optics, "HEALON5 OVD," 2004, [online]. Retrieved from the Interent: URL: http://abbottmedicaloptics.com/products/cataract/ovds/healon5-viscoelastic. Retrieved from the Internet on: Aug. 16, 2016, 5 pages.
(Continued)

*Primary Examiner* — Kami A Bosworth
(74) *Attorney, Agent, or Firm* — COOLEY LLP

(57) ABSTRACT

The present invention provides devices to access the suprachoroidal space or sub-retinal space in an eye via a minimally invasive transconjunctival approach. The devices may also be used after a partial dissection, for example after dissection of the outer scleral layer of the eye, and using the device within the dissection to access the suprachoroidal space or the sub-retinal space.

35 Claims, 8 Drawing Sheets

Related U.S. Application Data continuation of application No. 15/872,206, filed on Jan. 16, 2018, now Pat. No. 10,952,894, which is a continuation of application No. 14/821,310, filed on Aug. 7, 2015, now abandoned, which is a continuation of application No. 13/273,775, filed on Oct. 14, 2011, now abandoned.

(60) Provisional application No. 61/393,741, filed on Oct. 15, 2010.

(51) Int. Cl.
*A61M 5/46* (2006.01)
*A61M 5/48* (2006.01)
*A61M 5/31* (2006.01)

(52) U.S. Cl.
CPC .............. *A61M 5/46* (2013.01); *A61M 5/486* (2013.01); *A61M 2005/3103* (2013.01); *A61M 2210/0612* (2013.01)

(58) Field of Classification Search
CPC .. A61M 2025/0004; A61M 2210/0612; A61M 2005/3212; A61M 25/0618; A61M 25/0625; A61M 2025/0656; A61M 2025/0687; A61F 9/00; A61F 9/0017; A61F 9/007; A61F 9/00736; A61F 9/00781
See application file for complete search history.

(56) References Cited

U.S. PATENT DOCUMENTS

| | | | |
|---|---|---|---|
| 2,623,521 A * | 12/1952 | Shaw | A61M 5/32 604/170.02 |
| 2,841,145 A | 7/1958 | Epps | |
| 2,939,459 A | 6/1960 | Lazarte et al. | |
| 3,376,999 A | 4/1968 | De Hart et al. | |
| 3,477,432 A | 11/1969 | Shaw et al. | |
| 3,739,947 A | 6/1973 | Baumann et al. | |
| 3,762,540 A | 10/1973 | Baumann et al. | |
| 3,788,320 A | 1/1974 | Dye | |
| 3,838,690 A | 10/1974 | Friedman | |
| 3,892,311 A | 7/1975 | Sneider | |
| 3,962,430 A | 6/1976 | O'Neill | |
| 3,964,482 A | 6/1976 | Gerstel et al. | |
| 4,226,328 A | 10/1980 | Beddow | |
| 4,230,112 A | 10/1980 | Smith | |
| 4,303,071 A | 12/1981 | Smith | |
| 4,317,448 A | 3/1982 | Smith | |
| 4,377,897 A | 3/1983 | Eichenbaum et al. | |
| 4,383,530 A | 5/1983 | Bruno | |
| 4,417,887 A | 11/1983 | Koshi | |
| 4,432,964 A | 2/1984 | Shell et al. | |
| 4,501,363 A | 2/1985 | Isbey, Jr. | |
| 4,525,346 A | 6/1985 | Stark | |
| 4,564,016 A | 1/1986 | Maurice et al. | |
| 4,573,993 A | 3/1986 | Hoag et al. | |
| 4,601,708 A | 7/1986 | Jordan | |
| 4,615,331 A | 10/1986 | Kramann | |
| 4,627,841 A | 12/1986 | Dorr | |
| 4,662,870 A * | 5/1987 | Augustine | A61M 25/06 604/117 |
| 4,662,878 A | 5/1987 | Lindmayer | |
| 4,689,040 A | 8/1987 | Thompson | |
| 4,708,147 A | 11/1987 | Haaga | |
| 4,717,383 A | 1/1988 | Phillips et al. | |
| 4,736,850 A | 4/1988 | Bowman et al. | |
| 4,755,169 A | 7/1988 | Sarnoff et al. | |
| 4,795,432 A | 1/1989 | Karczmer | |
| 4,804,371 A | 2/1989 | Vaillancourt | |
| 4,826,490 A | 5/1989 | Byrne et al. | |
| 4,826,871 A | 5/1989 | Gressel et al. | |
| 4,883,483 A | 11/1989 | Lindmayer | |
| 4,889,529 A | 12/1989 | Haindl | |
| 4,941,874 A | 7/1990 | Sandow et al. | |
| 4,966,773 A | 10/1990 | Gressel et al. | |
| 5,015,240 A | 5/1991 | Soproni et al. | |
| 5,023,087 A | 6/1991 | Yau-Young | |
| 5,024,662 A | 6/1991 | Menes et al. | |
| 5,025,811 A | 6/1991 | Dobrogowski et al. | |
| 5,057,072 A | 10/1991 | Phipps | |
| 5,066,276 A | 11/1991 | Wang | |
| 5,098,389 A | 3/1992 | Cappucci | |
| 5,100,394 A | 3/1992 | Dudar et al. | |
| 5,104,381 A * | 4/1992 | Gresl | A61B 1/00135 D24/146 |
| 5,137,447 A | 8/1992 | Hunter | |
| 5,137,509 A | 8/1992 | Freitas | |
| 5,164,188 A | 11/1992 | Wong | |
| 5,172,807 A | 12/1992 | Dragan et al. | |
| 5,181,909 A | 1/1993 | McFarlane | |
| 5,206,267 A | 4/1993 | Shulman | |
| 5,211,638 A | 5/1993 | Dudar et al. | |
| 5,273,530 A | 12/1993 | Del Cerro et al. | |
| 5,279,564 A | 1/1994 | Taylor | |
| 5,284,474 A * | 2/1994 | Adair | A61B 17/3496 604/164.12 |
| 5,292,310 A * | 3/1994 | Yoon | A61B 17/3496 604/158 |
| 5,295,972 A | 3/1994 | Mischenko | |
| 5,295,974 A | 3/1994 | O'Laughlin | |
| 5,300,084 A | 4/1994 | Johnson | |
| 5,312,361 A | 5/1994 | Zadini et al. | |
| 5,320,609 A | 6/1994 | Haber et al. | |
| 5,354,286 A | 10/1994 | Mesa et al. | |
| 5,358,489 A | 10/1994 | Wyrick | |
| 5,364,373 A | 11/1994 | Waskonig et al. | |
| 5,364,374 A | 11/1994 | Morrison et al. | |
| 5,364,734 A | 11/1994 | Pawlowski et al. | |
| 5,395,310 A | 3/1995 | Untereker et al. | |
| 5,397,313 A | 3/1995 | Gross | |
| 5,399,159 A | 3/1995 | Chin et al. | |
| 5,401,247 A * | 3/1995 | Yoon | A61B 10/0233 604/185 |
| 5,407,070 A | 4/1995 | Bascos et al. | |
| 5,409,457 A | 4/1995 | Del Cerro et al. | |
| 5,443,505 A | 8/1995 | Wong et al. | |
| 5,454,409 A | 10/1995 | McAffer et al. | |
| 5,527,306 A | 6/1996 | Haining | |
| 5,538,503 A | 7/1996 | Henley | |
| 5,547,467 A | 8/1996 | Pliquett et al. | |
| 5,575,780 A | 11/1996 | Saito | |
| 5,632,740 A | 5/1997 | Koch et al. | |
| 5,658,256 A | 8/1997 | Shields | |
| D383,049 S | 9/1997 | Concari et al. | |
| 5,667,491 A | 9/1997 | Pliquett et al. | |
| 5,681,825 A | 10/1997 | Lindqvist et al. | |
| 5,752,942 A | 5/1998 | Doyle et al. | |
| 5,766,198 A | 6/1998 | Li | |
| 5,766,242 A | 6/1998 | Wong et al. | |
| 5,767,079 A | 6/1998 | Glaser et al. | |
| 5,779,668 A | 7/1998 | Grabenkort | |
| 5,788,679 A | 8/1998 | Gravlee, Jr. | |
| 5,792,099 A | 8/1998 | DeCamp et al. | |
| 5,817,075 A | 10/1998 | Giungo | |
| 5,824,072 A | 10/1998 | Wong | |
| 5,839,715 A | 11/1998 | Leinsing | |
| 5,893,397 A | 4/1999 | Peterson et al. | |
| 5,911,223 A | 6/1999 | Weaver et al. | |
| 5,919,158 A | 7/1999 | Saperstein et al. | |
| 5,951,520 A * | 9/1999 | Burzynski | A61M 25/0643 604/161 |
| 5,952,378 A | 9/1999 | Stjernschantz et al. | |
| 5,968,022 A | 10/1999 | Saito | |
| 6,003,566 A | 12/1999 | Thibault et al. | |
| 6,039,093 A | 3/2000 | Mrotzek et al. | |
| 6,059,111 A | 5/2000 | Davila et al. | |
| 6,083,199 A | 7/2000 | Thorley et al. | |
| 6,139,534 A | 10/2000 | Niedospial, Jr. et al. | |
| 6,143,329 A | 11/2000 | Kim | |
| 6,149,623 A | 11/2000 | Reynolds | |
| 6,154,671 A | 11/2000 | Parel et al. | |

(56) References Cited

U.S. PATENT DOCUMENTS

| | | | |
|---|---|---|---|
| 6,159,218 A | 12/2000 | Aramant et al. |
| 6,189,580 B1 | 2/2001 | Thibault et al. |
| 6,209,738 B1 | 4/2001 | Jansen et al. |
| 6,258,078 B1 | 7/2001 | Thilly |
| 6,280,470 B1 | 8/2001 | Peyman |
| 6,299,603 B1 | 10/2001 | Hecker et al. |
| 6,309,347 B1 | 10/2001 | Takahashi et al. |
| 6,309,374 B1 | 10/2001 | Hecker et al. |
| 6,319,225 B1 | 11/2001 | Sugita et al. |
| 6,319,240 B1 | 11/2001 | Beck |
| 6,334,856 B1 | 1/2002 | Allen et al. |
| 6,378,526 B1 | 4/2002 | Bowman et al. |
| 6,378,714 B1 | 4/2002 | Jansen et al. |
| 6,379,340 B1 | 4/2002 | Zinger et al. |
| 6,387,078 B1 | 5/2002 | Gillespie, III |
| 6,397,849 B1 | 6/2002 | Bowman et al. |
| 6,413,245 B1 | 7/2002 | Yaacobi et al. |
| 6,432,090 B1 | 8/2002 | Brunel |
| 6,491,670 B1 | 12/2002 | Toth et al. |
| 6,494,865 B1 | 12/2002 | Alchas |
| 6,503,231 B1 | 1/2003 | Prausnitz et al. |
| 6,503,240 B1 | 1/2003 | Niedospial, Jr. et al. |
| 6,517,523 B1 | 2/2003 | Kaneko et al. |
| 6,524,581 B1 | 2/2003 | Adamis |
| 6,530,904 B1 | 3/2003 | Edwards et al. |
| 6,540,725 B1 | 4/2003 | Ponzi |
| 6,544,246 B1 | 4/2003 | Niedospial, Jr. |
| 6,546,283 B1 | 4/2003 | Beck et al. |
| 6,551,299 B2 | 4/2003 | Miyoshi et al. |
| 6,558,361 B1 | 5/2003 | Yeshurun |
| 6,564,630 B1 | 5/2003 | Klemp |
| 6,568,439 B1 | 5/2003 | Se et al. |
| 6,569,123 B2 | 5/2003 | Alchas et al. |
| 6,571,837 B2 | 6/2003 | Jansen et al. |
| 6,589,202 B1 | 7/2003 | Powell |
| 6,601,721 B2 | 8/2003 | Jansen et al. |
| 6,611,707 B1 | 8/2003 | Prausnitz et al. |
| 6,622,864 B1 | 9/2003 | Debbs et al. |
| 6,626,309 B1 | 9/2003 | Jansen et al. |
| 6,638,244 B1 | 10/2003 | Reynolds |
| 6,656,433 B2 | 12/2003 | Sasso |
| 6,715,520 B2 | 4/2004 | Andreasson et al. |
| 6,729,370 B2 | 5/2004 | Norton et al. |
| 6,738,526 B1 | 5/2004 | Betrisey et al. |
| 6,743,211 B1 | 6/2004 | Prausnitz et al. |
| 6,773,916 B1 | 8/2004 | Thiel et al. |
| D499,153 S | 11/2004 | Kuo |
| 6,832,994 B2 | 12/2004 | Niedospial, Jr. et al. |
| 6,875,205 B2 | 4/2005 | Leinsing |
| 6,883,222 B2 | 4/2005 | Landau |
| 6,918,889 B1 | 7/2005 | Brunel |
| 6,929,623 B2 | 8/2005 | Stone |
| 6,936,053 B1 | 8/2005 | Weiss |
| 6,957,745 B2 | 10/2005 | Thibault et al. |
| 6,979,316 B1 | 12/2005 | Rubin et al. |
| 6,997,917 B2 | 2/2006 | Niedospial, Jr. et al. |
| 7,025,389 B2 | 4/2006 | Cuschieri et al. |
| 7,025,774 B2 | 4/2006 | Freeman et al. |
| 7,150,735 B2 | 12/2006 | Hickle |
| 7,207,965 B2 | 4/2007 | Simon |
| 7,207,980 B2 | 4/2007 | Christian et al. |
| 7,211,062 B2 | 5/2007 | Kwon |
| 7,214,212 B2 | 5/2007 | Pommereau et al. |
| 7,226,439 B2 | 6/2007 | Prausnitz et al. |
| 7,316,676 B2 | 1/2008 | Peyman et al. |
| 7,326,194 B2 | 2/2008 | Zinger et al. |
| 7,425,207 B2 | 9/2008 | Miller et al. |
| 7,435,237 B2 | 10/2008 | Tan |
| 7,468,057 B2 | 12/2008 | Ponzi |
| 7,470,257 B2 | 12/2008 | Norton et al. |
| 7,488,308 B2 | 2/2009 | Lesch, Jr. |
| 7,510,547 B2 | 3/2009 | Fangrow |
| 7,510,548 B2 | 3/2009 | Fangrow |
| D590,690 S | 4/2009 | Bertini |
| D598,543 S | 8/2009 | Vogel et al. |
| 7,569,035 B1 | 8/2009 | Wilmot et al. |
| 7,615,041 B2 | 11/2009 | Sullivan et al. |
| 7,632,261 B2 | 12/2009 | Zinger et al. |
| 7,648,482 B2 | 1/2010 | Edwards et al. |
| 7,648,491 B2 | 1/2010 | Rogers |
| 7,678,077 B2 | 3/2010 | Harris et al. |
| 7,678,078 B1 | 3/2010 | Peyman et al. |
| 7,722,581 B2 | 5/2010 | Peyman |
| 7,799,009 B2 | 9/2010 | Niedospial, Jr. et al. |
| 7,879,018 B2 | 2/2011 | Zinger et al. |
| 7,914,803 B2 | 3/2011 | Chowhan et al. |
| 7,918,814 B2 | 4/2011 | Prausnitz et al. |
| 7,918,874 B2 | 4/2011 | Siegal |
| 7,947,660 B2 | 5/2011 | Clark et al. |
| 7,967,772 B2 | 6/2011 | McKenzie et al. |
| 7,975,733 B2 | 7/2011 | Horppu et al. |
| 7,981,101 B2 | 7/2011 | Walsh |
| 8,003,124 B2 | 8/2011 | Varner et al. |
| 8,009,162 B2 | 8/2011 | Takatori |
| 8,016,809 B2 | 9/2011 | Zinger et al. |
| 8,025,653 B2 | 9/2011 | Capitaine et al. |
| 8,034,105 B2 | 10/2011 | Stegmann et al. |
| 8,070,739 B2 | 12/2011 | Zinger et al. |
| 8,099,162 B2 | 1/2012 | Roy |
| 8,114,110 B2 | 2/2012 | Bednarek et al. |
| 8,123,729 B2 | 2/2012 | Yamamoto et al. |
| 8,123,736 B2 | 2/2012 | Kraushaar et al. |
| 8,128,960 B2 | 3/2012 | Kabra et al. |
| 8,137,312 B2 | 3/2012 | Sundar et al. |
| 8,157,784 B2 | 4/2012 | Rogers |
| 8,162,914 B2 | 4/2012 | Kraushaar et al. |
| 8,167,863 B2 | 5/2012 | Yow |
| 8,172,830 B2 | 5/2012 | Christian et al. |
| 8,173,617 B2 | 5/2012 | Clark et al. |
| 8,177,768 B2 | 5/2012 | Leinsing |
| 8,187,248 B2 | 5/2012 | Zihlmann |
| 8,192,408 B2 | 6/2012 | Nazzaro et al. |
| 8,197,435 B2 | 6/2012 | Prausnitz et al. |
| 8,197,443 B2 | 6/2012 | Sundar et al. |
| 8,197,459 B2 | 6/2012 | Jansen et al. |
| 8,221,353 B2 | 7/2012 | Cormier et al. |
| 8,225,826 B2 | 7/2012 | Horppu et al. |
| 8,235,967 B2 | 8/2012 | Chevallier et al. |
| D667,111 S | 9/2012 | Robinson |
| 8,257,336 B2 | 9/2012 | Zihlmann |
| 8,262,641 B2 | 9/2012 | Vedrine et al. |
| 8,287,494 B2 | 10/2012 | Ma |
| 8,303,599 B2 | 11/2012 | Hess et al. |
| D672,506 S | 12/2012 | Szymanski |
| 8,323,227 B2 | 12/2012 | Hamatake et al. |
| 8,328,772 B2 | 12/2012 | Kinast et al. |
| 8,337,421 B2 | 12/2012 | Freeman et al. |
| 8,337,509 B2 | 12/2012 | Schieber et al. |
| 8,348,924 B2 | 1/2013 | Christian et al. |
| 8,403,941 B2 | 3/2013 | Peterson et al. |
| 8,409,165 B2 | 4/2013 | Niedospial, Jr. et al. |
| 8,425,473 B2 | 4/2013 | Ho et al. |
| 8,430,862 B2 | 4/2013 | Peyman et al. |
| 8,448,786 B2 | 5/2013 | Tomes et al. |
| 8,460,242 B2 | 6/2013 | Paques et al. |
| 8,469,939 B2 | 6/2013 | Fangrow, Jr. |
| 8,475,404 B2 | 7/2013 | Foshee et al. |
| 8,480,646 B2 | 7/2013 | Nord et al. |
| 8,506,515 B2 | 8/2013 | Burns et al. |
| 8,512,309 B2 | 8/2013 | Shemesh et al. |
| 8,529,492 B2 | 9/2013 | Clauson et al. |
| 8,535,333 B2 | 9/2013 | De Juan, Jr. et al. |
| 8,540,692 B2 | 9/2013 | Fangrow |
| 8,545,430 B2 | 10/2013 | Silvestrini |
| 8,545,554 B2 | 10/2013 | Novakovic et al. |
| 8,562,545 B2 | 10/2013 | Freeman et al. |
| 8,571,802 B2 | 10/2013 | Robinson et al. |
| 8,574,214 B2 | 11/2013 | Kuhn et al. |
| 8,574,217 B2 | 11/2013 | Peyman |
| 8,602,959 B1 | 12/2013 | Park et al. |
| 8,608,723 B2 | 12/2013 | Lev et al. |
| 8,617,121 B2 | 12/2013 | Lanin et al. |
| 8,628,508 B2 | 1/2014 | Weitzel et al. |
| 8,632,589 B2 | 1/2014 | Helmy |

(56) References Cited

U.S. PATENT DOCUMENTS

| | | |
|---|---|---|
| 8,636,713 B2 | 1/2014 | Prausnitz et al. |
| 8,652,118 B2 | 2/2014 | Peyman |
| 8,663,167 B2 | 3/2014 | Bartha |
| 8,663,303 B2 | 3/2014 | Horvath et al. |
| 8,668,676 B2 | 3/2014 | Chang |
| 8,685,435 B2 | 4/2014 | Nivaggioli et al. |
| 8,702,659 B2 | 4/2014 | Lanin et al. |
| 8,727,117 B2 | 5/2014 | Maasarani |
| 8,747,365 B2 | 6/2014 | De Sausmarez Lintell |
| 8,752,598 B2 | 6/2014 | Denenburg et al. |
| 8,758,306 B2 | 6/2014 | Lopez et al. |
| 8,795,226 B2 | 8/2014 | Kuhn et al. |
| 8,808,225 B2 | 8/2014 | Prausnitz et al. |
| 8,808,242 B2 | 8/2014 | Paques et al. |
| D713,958 S | 9/2014 | Srinivasan et al. |
| 8,821,870 B2 | 9/2014 | Robinson et al. |
| D715,125 S | 10/2014 | Hung |
| 8,852,137 B2 | 10/2014 | Horvath et al. |
| 8,864,740 B2 | 10/2014 | Schabbach et al. |
| D718,602 S | 12/2014 | Musser |
| D719,256 S | 12/2014 | Ohashi |
| 8,920,375 B2 | 12/2014 | Gonnelli |
| D726,908 S | 4/2015 | Yu et al. |
| D733,289 S | 6/2015 | Blanchard et al. |
| D740,098 S | 10/2015 | Kuo et al. |
| 9,180,044 B2 | 11/2015 | Touchard et al. |
| 9,180,047 B2 | 11/2015 | Andino et al. |
| D750,223 S | 2/2016 | Andino et al. |
| 9,539,139 B2 | 1/2017 | Andino et al. |
| 9,572,800 B2 | 2/2017 | Zarnitsyn et al. |
| 9,636,253 B1 | 5/2017 | Andino et al. |
| 9,636,332 B2 | 5/2017 | Zarnitsyn et al. |
| 9,664,926 B2 | 5/2017 | Mitsui |
| 9,770,361 B2 | 9/2017 | Andino et al. |
| 9,788,995 B2 | 10/2017 | Prausnitz et al. |
| 9,931,330 B2 | 4/2018 | Zarnitsyn et al. |
| 9,937,075 B2 | 4/2018 | Andino et al. |
| 9,956,114 B2 | 5/2018 | Andino et al. |
| 10,188,550 B2 | 1/2019 | Andino et al. |
| 10,390,901 B2 | 8/2019 | Godfrey et al. |
| 10,517,756 B2 | 12/2019 | Andino et al. |
| 10,555,833 B2 | 2/2020 | Andino et al. |
| 10,632,013 B2 | 4/2020 | Prausnitz et al. |
| 10,722,396 B2 | 7/2020 | Andino et al. |
| 10,905,586 B2 | 2/2021 | Prausnitz et al. |
| 10,952,894 B2 | 3/2021 | Hammack et al. |
| 10,973,681 B2 | 4/2021 | Andino et al. |
| 11,559,428 B2 | 1/2023 | Andino et al. |
| 11,596,545 B2 | 3/2023 | Andino et al. |
| 11,752,101 B2 | 9/2023 | Yamamoto et al. |
| 2001/0008961 A1 | 7/2001 | Hecker et al. |
| 2001/0044604 A1* | 11/2001 | Luther ............ A61M 25/0068 604/164.06 |
| 2001/0051798 A1 | 12/2001 | Hochman |
| 2002/0042594 A1 | 4/2002 | Lum et al. |
| 2002/0052580 A1 | 5/2002 | Ooyauchi |
| 2002/0082527 A1 | 6/2002 | Liu et al. |
| 2002/0082543 A1 | 6/2002 | Park et al. |
| 2002/0108875 A1 | 8/2002 | Feinberg et al. |
| 2002/0112981 A1 | 8/2002 | Cooper et al. |
| 2002/0142459 A1 | 10/2002 | Williams et al. |
| 2002/0156413 A1 | 10/2002 | Williams et al. |
| 2003/0009113 A1 | 1/2003 | Olson |
| 2003/0050602 A1 | 3/2003 | Pettis et al. |
| 2003/0083645 A1 | 5/2003 | Angel et al. |
| 2003/0088204 A1 | 5/2003 | Joshi |
| 2003/0139729 A1 | 7/2003 | Stegmann et al. |
| 2003/0171722 A1 | 9/2003 | Paques et al. |
| 2003/0233070 A1 | 12/2003 | De La Serna et al. |
| 2004/0019331 A1 | 1/2004 | Yeshurun |
| 2004/0039253 A1 | 2/2004 | Peyman et al. |
| 2004/0049150 A1 | 3/2004 | Dalton et al. |
| 2004/0059256 A1 | 3/2004 | Perez |
| 2004/0072105 A1 | 4/2004 | Yeshurun et al. |
| 2004/0106904 A1 | 6/2004 | Gonnelli et al. |
| 2004/0122359 A1 | 6/2004 | Wenz et al. |
| 2004/0141925 A1 | 7/2004 | Bosch et al. |
| 2004/0164454 A1 | 8/2004 | Gartstein et al. |
| 2004/0186084 A1 | 9/2004 | Alam et al. |
| 2004/0199130 A1 | 10/2004 | Chornenky et al. |
| 2004/0215347 A1 | 10/2004 | Hayes |
| 2004/0249404 A1 | 12/2004 | Haefliger |
| 2004/0265365 A1 | 12/2004 | Daddona et al. |
| 2005/0009910 A1 | 1/2005 | Hughes et al. |
| 2005/0033230 A1 | 2/2005 | Alchas et al. |
| 2005/0055083 A1 | 3/2005 | Carranza et al. |
| 2005/0065137 A1 | 3/2005 | Jani et al. |
| 2005/0070819 A1 | 3/2005 | Poux et al. |
| 2005/0089545 A1 | 4/2005 | Kuwano et al. |
| 2005/0096594 A1* | 5/2005 | Deslauriers ......... A61M 25/06 604/164.01 |
| 2005/0101582 A1 | 5/2005 | Lyons et al. |
| 2005/0101882 A1 | 5/2005 | Leira et al. |
| 2005/0101967 A1 | 5/2005 | Weber et al. |
| 2005/0137525 A1 | 6/2005 | Wang et al. |
| 2005/0148034 A1 | 7/2005 | Hariri et al. |
| 2005/0171507 A1 | 8/2005 | Christian et al. |
| 2005/0181017 A1 | 8/2005 | Hughes et al. |
| 2005/0203575 A1 | 9/2005 | Carson et al. |
| 2005/0209565 A1 | 9/2005 | Yuzhakov et al. |
| 2005/0244462 A1 | 11/2005 | Farooq |
| 2005/0244463 A1 | 11/2005 | Huang et al. |
| 2005/0244469 A1 | 11/2005 | Whitcup et al. |
| 2005/0245906 A1 | 11/2005 | Makower et al. |
| 2005/0256499 A1 | 11/2005 | Pettis et al. |
| 2005/0281862 A1 | 12/2005 | Karakelle et al. |
| 2006/0013859 A1 | 1/2006 | Yamada et al. |
| 2006/0032768 A1 | 2/2006 | Hamai et al. |
| 2006/0036318 A1 | 2/2006 | Foulkes |
| 2006/0055090 A1 | 3/2006 | Lee et al. |
| 2006/0084942 A1 | 4/2006 | Kim et al. |
| 2006/0086689 A1 | 4/2006 | Raju |
| 2006/0089607 A1 | 4/2006 | Chen |
| 2006/0141049 A1 | 6/2006 | Lyons et al. |
| 2006/0173418 A1 | 8/2006 | Rinaudo et al. |
| 2006/0178614 A1 | 8/2006 | Nemati |
| 2006/0189608 A1 | 8/2006 | Bingaman |
| 2006/0195187 A1 | 8/2006 | Stegmann et al. |
| 2006/0202385 A1 | 9/2006 | Xu et al. |
| 2006/0229562 A1 | 10/2006 | Marsh et al. |
| 2006/0233858 A1 | 10/2006 | Tzekov et al. |
| 2006/0259008 A1 | 11/2006 | Orilla |
| 2006/0271025 A1 | 11/2006 | Jones et al. |
| 2007/0016103 A1 | 1/2007 | Calasso et al. |
| 2007/0060927 A1 | 3/2007 | Longson et al. |
| 2007/0073197 A1 | 3/2007 | Prausnitz et al. |
| 2007/0082841 A1 | 4/2007 | Higuchi et al. |
| 2007/0093742 A1 | 4/2007 | Higuchi et al. |
| 2007/0093877 A1 | 4/2007 | Beecham et al. |
| 2007/0129693 A1 | 6/2007 | Hunter et al. |
| 2007/0149944 A1 | 6/2007 | Tashiro et al. |
| 2007/0151882 A1 | 7/2007 | Cocheteux et al. |
| 2007/0178197 A1 | 8/2007 | LaRue et al. |
| 2007/0191863 A1 | 8/2007 | De Juan, Jr. et al. |
| 2007/0202116 A1 | 8/2007 | Burnie et al. |
| 2007/0202186 A1 | 8/2007 | Yamamoto et al. |
| 2007/0224278 A1 | 9/2007 | Lyons et al. |
| 2007/0225654 A1 | 9/2007 | Hess et al. |
| 2007/0233037 A1 | 10/2007 | Gifford, III et al. |
| 2007/0260201 A1 | 11/2007 | Prausnitz et al. |
| 2007/0270745 A1 | 11/2007 | Nezhat et al. |
| 2007/0270768 A1 | 11/2007 | Dacquay et al. |
| 2007/0282405 A1 | 12/2007 | Wong, Jr. et al. |
| 2007/0287985 A1 | 12/2007 | Estes et al. |
| 2007/0299386 A1 | 12/2007 | Peyman |
| 2008/0008762 A1 | 1/2008 | Robinson et al. |
| 2008/0015539 A1 | 1/2008 | Pieroni et al. |
| 2008/0027371 A1 | 1/2008 | Higuchi et al. |
| 2008/0033351 A1 | 2/2008 | Trogden et al. |
| 2008/0058704 A1 | 3/2008 | Hee et al. |
| 2008/0058717 A1 | 3/2008 | Spector |
| 2008/0065002 A1 | 3/2008 | Lobl et al. |
| 2008/0071246 A1 | 3/2008 | Nazzaro et al. |
| 2008/0082841 A1 | 4/2008 | Juenemann et al. |

(56) References Cited

U.S. PATENT DOCUMENTS

| | | |
|---|---|---|
| 2008/0097335 A1 | 4/2008 | Trogden et al. |
| 2008/0097346 A1 | 4/2008 | Charles |
| 2008/0097390 A1 | 4/2008 | Dacquay et al. |
| 2008/0131484 A1 | 6/2008 | Robinson et al. |
| 2008/0152694 A1 | 6/2008 | Lobl et al. |
| 2008/0177239 A1 | 7/2008 | Li et al. |
| 2008/0183123 A1 | 7/2008 | Behar-Cohen et al. |
| 2008/0200883 A1 | 8/2008 | Tomono |
| 2008/0208255 A1 | 8/2008 | Siegal |
| 2008/0228127 A1 | 9/2008 | Burns et al. |
| 2008/0234625 A1 | 9/2008 | Dacquay et al. |
| 2008/0300634 A1 | 12/2008 | Gray |
| 2009/0030381 A1 | 1/2009 | Lind et al. |
| 2009/0076463 A1 | 3/2009 | Attinger |
| 2009/0081277 A1 | 3/2009 | Robinson et al. |
| 2009/0082321 A1 | 3/2009 | Edelman et al. |
| 2009/0082713 A1 | 3/2009 | Friden |
| 2009/0088721 A1 | 4/2009 | De Bizemont et al. |
| 2009/0105749 A1 | 4/2009 | De Juan et al. |
| 2009/0148527 A1 | 6/2009 | Robinson et al. |
| 2009/0187167 A1 | 7/2009 | Sexton et al. |
| 2009/0259180 A1 | 10/2009 | Choi |
| 2009/0287161 A1 | 11/2009 | Traub et al. |
| 2009/0312782 A1 | 12/2009 | Park |
| 2010/0010004 A1 | 1/2010 | Van Emelen et al. |
| 2010/0010452 A1 | 1/2010 | Paques et al. |
| 2010/0012537 A1 | 1/2010 | Farrar et al. |
| 2010/0015158 A1 | 1/2010 | Robinson et al. |
| 2010/0030150 A1 | 2/2010 | Paques et al. |
| 2010/0057011 A1 | 3/2010 | Charles |
| 2010/0074925 A1 | 3/2010 | Carmon |
| 2010/0074957 A1 | 3/2010 | Robinson et al. |
| 2010/0081707 A1* | 4/2010 | Ali ............... A61P 27/02 604/151 |
| 2010/0098772 A1 | 4/2010 | Robinson et al. |
| 2010/0100054 A1 | 4/2010 | Cormier et al. |
| 2010/0152646 A1 | 6/2010 | Girijavallabhan et al. |
| 2010/0152667 A1 | 6/2010 | Kietzmann |
| 2010/0152676 A1 | 6/2010 | Clements et al. |
| 2010/0160889 A1 | 6/2010 | Smith et al. |
| 2010/0173866 A1 | 7/2010 | Hee et al. |
| 2010/0191176 A1 | 7/2010 | Ho et al. |
| 2010/0191177 A1* | 7/2010 | Chang ............ A61F 9/00736 604/22 |
| 2010/0211079 A1 | 8/2010 | Aramant |
| 2010/0241102 A1 | 9/2010 | Ma |
| 2010/0256597 A1 | 10/2010 | Prausnitz et al. |
| 2010/0312120 A1 | 12/2010 | Meier |
| 2010/0318034 A1 | 12/2010 | Goncalves |
| 2011/0004265 A1 | 1/2011 | Wenger et al. |
| 2011/0022023 A1 | 1/2011 | Weitzel et al. |
| 2011/0060310 A1 | 3/2011 | Prestrelski et al. |
| 2011/0112546 A1 | 5/2011 | Juan, Jr. et al. |
| 2011/0152775 A1 | 6/2011 | Lopez et al. |
| 2011/0166531 A1 | 7/2011 | Stroumpoulis et al. |
| 2011/0202012 A1 | 8/2011 | Bartlett |
| 2011/0213317 A1 | 9/2011 | Chen et al. |
| 2011/0238075 A1 | 9/2011 | Clauson et al. |
| 2011/0243999 A1 | 10/2011 | Dellamary et al. |
| 2011/0264028 A1 | 10/2011 | Ramdas et al. |
| 2011/0282298 A1 | 11/2011 | Agian et al. |
| 2011/0288492 A1 | 11/2011 | Holmqvist |
| 2011/0295152 A1 | 12/2011 | Sasaki et al. |
| 2011/0306923 A1 | 12/2011 | Roy |
| 2012/0004245 A1 | 1/2012 | May et al. |
| 2012/0008327 A1 | 1/2012 | Brennan et al. |
| 2012/0024987 A1 | 2/2012 | Nagele Nacken |
| 2012/0029360 A1 | 2/2012 | Hendriks et al. |
| 2012/0035524 A1 | 2/2012 | Silvestrini |
| 2012/0059346 A1 | 3/2012 | Sheppard et al. |
| 2012/0078224 A1 | 3/2012 | Lerner et al. |
| 2012/0083727 A1 | 4/2012 | Barnett |
| 2012/0095414 A1 | 4/2012 | Lanin et al. |
| 2012/0095438 A1 | 4/2012 | Lanin et al. |
| 2012/0101475 A1 | 4/2012 | Wilmot et al. |
| 2012/0116306 A1 | 5/2012 | Heald et al. |
| 2012/0123351 A1 | 5/2012 | Lanin et al. |
| 2012/0123386 A1 | 5/2012 | Tsals |
| 2012/0123437 A1 | 5/2012 | Horvath et al. |
| 2012/0123440 A1 | 5/2012 | Horvath et al. |
| 2012/0123473 A1 | 5/2012 | Hernandez |
| 2012/0130207 A1 | 5/2012 | O'Dea et al. |
| 2012/0136318 A1 | 5/2012 | Lanin et al. |
| 2012/0150128 A1 | 6/2012 | Zhao |
| 2012/0157880 A1 | 6/2012 | Haselby et al. |
| 2012/0165723 A1 | 6/2012 | Horvath et al. |
| 2012/0191064 A1 | 7/2012 | Conston et al. |
| 2012/0197208 A1 | 8/2012 | Bruggemann et al. |
| 2012/0197218 A1 | 8/2012 | Timm |
| 2012/0203193 A1 | 8/2012 | Rogers |
| 2012/0220917 A1 | 8/2012 | Silvestrini et al. |
| 2012/0226260 A1 | 9/2012 | Prausnitz et al. |
| 2012/0232522 A1 | 9/2012 | Prausnitz et al. |
| 2012/0259288 A1 | 10/2012 | Wagner et al. |
| 2012/0265149 A1 | 10/2012 | Lerner et al. |
| 2012/0271272 A1 | 10/2012 | Hammack et al. |
| 2012/0296307 A1 | 11/2012 | Holt et al. |
| 2013/0035662 A1 | 2/2013 | Decker et al. |
| 2013/0040895 A1 | 2/2013 | Robinson et al. |
| 2013/0041265 A1 | 2/2013 | Sostek et al. |
| 2013/0060202 A1 | 3/2013 | Thorley et al. |
| 2013/0065888 A1 | 3/2013 | Cetina-Cizmek et al. |
| 2013/0072900 A1 | 3/2013 | Colantonio |
| 2013/0079716 A1 | 3/2013 | Thorley et al. |
| 2013/0096533 A1 | 4/2013 | Freeman et al. |
| 2013/0102973 A1 | 4/2013 | Thorley et al. |
| 2013/0116523 A1 | 5/2013 | Jung, II et al. |
| 2013/0138049 A1 | 5/2013 | Kemp et al. |
| 2013/0140208 A1 | 6/2013 | Hemmann |
| 2013/0150803 A1 | 6/2013 | Shetty et al. |
| 2013/0190694 A1 | 7/2013 | Barrow-Williams et al. |
| 2013/0211335 A1 | 8/2013 | Paques et al. |
| 2013/0216623 A1 | 8/2013 | Yamamoto et al. |
| 2013/0218102 A1 | 8/2013 | Iwase et al. |
| 2013/0218269 A1 | 8/2013 | Schachar et al. |
| 2013/0226103 A1 | 8/2013 | Papiorek |
| 2013/0237910 A1 | 9/2013 | Shetty et al. |
| 2013/0237916 A1 | 9/2013 | Hanson et al. |
| 2013/0245600 A1 | 9/2013 | Yamamoto et al. |
| 2013/0253416 A1 | 9/2013 | Rotenstreich |
| 2013/0289545 A1 | 10/2013 | Baerveldt et al. |
| 2013/0295006 A1 | 11/2013 | Christoforidis et al. |
| 2013/0331786 A1 | 12/2013 | Hofmann |
| 2013/0338612 A1 | 12/2013 | Smith et al. |
| 2014/0010823 A1 | 1/2014 | Robinson et al. |
| 2014/0012226 A1 | 1/2014 | Hochman |
| 2014/0018771 A1 | 1/2014 | Shekalim |
| 2014/0027326 A1 | 1/2014 | Peruzzo |
| 2014/0031833 A1 | 1/2014 | Novakovic et al. |
| 2014/0039391 A1 | 2/2014 | Clarke et al. |
| 2014/0039413 A1 | 2/2014 | Jugl et al. |
| 2014/0078854 A1 | 3/2014 | Head et al. |
| 2014/0088552 A1 | 3/2014 | Soni et al. |
| 2014/0094752 A1 | 4/2014 | Hiles |
| 2014/0102927 A1 | 4/2014 | Liversidge |
| 2014/0107566 A1 | 4/2014 | Prausnitz et al. |
| 2014/0114243 A1 | 4/2014 | Smith et al. |
| 2014/0124528 A1 | 5/2014 | Fangrow |
| 2014/0135716 A1 | 5/2014 | Clarke et al. |
| 2014/0194834 A1 | 7/2014 | Passaglia |
| 2014/0200518 A1 | 7/2014 | Ekman et al. |
| 2014/0224688 A1 | 8/2014 | Slemmen et al. |
| 2014/0231287 A1 | 8/2014 | Tomes et al. |
| 2014/0236098 A1 | 8/2014 | Mica et al. |
| 2014/0243754 A1 | 8/2014 | Clarke et al. |
| 2014/0249539 A1 | 9/2014 | Mica et al. |
| 2014/0257207 A1 | 9/2014 | Clarke et al. |
| 2014/0261727 A1 | 9/2014 | Mansour et al. |
| 2014/0261877 A1 | 9/2014 | Ivosevic et al. |
| 2014/0276482 A1 | 9/2014 | Astafieva et al. |
| 2014/0276649 A1 | 9/2014 | Ivosevic et al. |
| 2014/0296802 A1 | 10/2014 | Geiger et al. |
| 2014/0309599 A1 | 10/2014 | Schaller |
| 2014/0323979 A1 | 10/2014 | Henley et al. |

(56) References Cited

U.S. PATENT DOCUMENTS

| | | |
|---|---|---|
| 2014/0323985 A1 | 10/2014 | Hourmand et al. |
| 2014/0330213 A1 | 11/2014 | Hourmand et al. |
| 2014/0350479 A1 | 11/2014 | Hourmand et al. |
| 2014/0353190 A1 | 12/2014 | Okihara et al. |
| 2015/0013827 A1 | 1/2015 | Kuhn |
| 2015/0013835 A1 | 1/2015 | Cordes |
| 2015/0025474 A1 | 1/2015 | Riedel et al. |
| 2015/0038905 A1 | 2/2015 | Andino et al. |
| 2015/0045731 A1 | 2/2015 | Gupta et al. |
| 2015/0045744 A1 | 2/2015 | Gupta et al. |
| 2015/0051545 A1 | 2/2015 | Henderson et al. |
| 2015/0051581 A1 | 2/2015 | Andino et al. |
| 2015/0110717 A1 | 4/2015 | Distel et al. |
| 2015/0129456 A1 | 5/2015 | Miller et al. |
| 2015/0133415 A1 | 5/2015 | Whitcup |
| 2015/0157359 A1 | 6/2015 | Shinzato et al. |
| 2015/0209180 A1 | 7/2015 | Prausnitz et al. |
| 2015/0223977 A1 | 8/2015 | Oberkircher et al. |
| 2015/0258120 A1 | 9/2015 | Zarnitsyn et al. |
| 2015/0297609 A1 | 10/2015 | Shah et al. |
| 2015/0320596 A1 | 11/2015 | Gifford, III et al. |
| 2016/0015895 A1 | 1/2016 | Blondino et al. |
| 2016/0015908 A1 | 1/2016 | Uemura et al. |
| 2016/0022486 A1 | 1/2016 | Clauson et al. |
| 2016/0106584 A1 | 4/2016 | Andino et al. |
| 2016/0106587 A1 | 4/2016 | Jarrett et al. |
| 2016/0166819 A1 | 6/2016 | Simmers |
| 2016/0193080 A1 | 7/2016 | Hammack et al. |
| 2016/0199581 A1 | 7/2016 | Cachemaille et al. |
| 2016/0206628 A1 | 7/2016 | Zarnitsyn et al. |
| 2016/0213662 A1 | 7/2016 | Zarnitsyn et al. |
| 2016/0310417 A1 | 10/2016 | Prausnitz et al. |
| 2016/0331738 A1 | 11/2016 | Jarrett et al. |
| 2016/0354239 A1 | 12/2016 | Roy |
| 2016/0354244 A1 | 12/2016 | Horvath et al. |
| 2017/0086725 A1 | 3/2017 | Woo et al. |
| 2017/0095369 A1 | 4/2017 | Andino et al. |
| 2017/0165109 A1 | 6/2017 | Gunn et al. |
| 2017/0216228 A1 | 8/2017 | Asgharian et al. |
| 2017/0224435 A1 | 8/2017 | Godfrey et al. |
| 2017/0224534 A1 | 8/2017 | Andino et al. |
| 2017/0273827 A1 | 9/2017 | Prausnitz et al. |
| 2017/0290702 A1 | 10/2017 | Yamamoto et al. |
| 2017/0333416 A1 | 11/2017 | Zarnitsyn et al. |
| 2017/0340560 A1 | 11/2017 | Yamamoto et al. |
| 2018/0028358 A1 | 2/2018 | Andino et al. |
| 2018/0028516 A1 | 2/2018 | Zarnitsyn et al. |
| 2018/0042765 A1 | 2/2018 | Noronha et al. |
| 2018/0042767 A1 | 2/2018 | Andino et al. |
| 2018/0092897 A1 | 4/2018 | Zarnitsyn et al. |
| 2018/0325884 A1 | 11/2018 | Zarnitsyn et al. |
| 2018/0333297 A1 | 11/2018 | Andino et al. |
| 2019/0000669 A1 | 1/2019 | Hammack et al. |
| 2019/0231592 A1 | 8/2019 | Andino et al. |
| 2019/0240208 A1 | 8/2019 | Zarnitsyn et al. |
| 2019/0269702 A1 | 9/2019 | White et al. |
| 2019/0290485 A1 | 9/2019 | Andino et al. |
| 2019/0307606 A1 | 10/2019 | Andino et al. |
| 2019/0350755 A1 | 11/2019 | Andino et al. |
| 2020/0030143 A1 | 1/2020 | Andino et al. |
| 2020/0061357 A1 | 2/2020 | Jung et al. |
| 2020/0237556 A1 | 7/2020 | Prausnitz et al. |
| 2020/0330269 A1 | 10/2020 | Bley et al. |
| 2020/0390692 A1 | 12/2020 | Yamamoto et al. |
| 2021/0022918 A1 | 1/2021 | Prausnitz et al. |
| 2021/0169689 A1 | 6/2021 | Bley et al. |
| 2021/0212940 A1 | 7/2021 | Yamamoto et al. |
| 2021/0220173 A1 | 7/2021 | Andino et al. |
| 2021/0366311 A1 | 11/2021 | Fisher et al. |
| 2021/0393436 A1 | 12/2021 | Prausnitz et al. |
| 2022/0062040 A1 | 3/2022 | Hammack et al. |
| 2022/0280386 A1 | 9/2022 | Andino et al. |
| 2022/0347014 A1 | 11/2022 | Yamamoto et al. |
| 2023/0157869 A1 | 5/2023 | Andino et al. |
| 2023/0363941 A1 | 11/2023 | Andino et al. |
| 2023/0372235 A1 | 11/2023 | Yamamoto |

FOREIGN PATENT DOCUMENTS

| | | | |
|---|---|---|---|
| CN | 1604799 A | 4/2005 | |
| CN | 1608587 A | 4/2005 | |
| CN | 1674954 A | 9/2005 | |
| CN | 1681547 A | 10/2005 | |
| CN | 1706365 A | 12/2005 | |
| CN | 1736474 A | 2/2006 | |
| CN | 1946445 A | 4/2007 | |
| CN | 101031256 A | 9/2007 | |
| CN | 101052434 A | 10/2007 | |
| CN | 101351239 A | 1/2009 | |
| CN | 201192452 Y | 2/2009 | |
| CN | 101559249 A | 10/2009 | |
| CN | 201356711 Y | 12/2009 | |
| CN | 201591741 U | 9/2010 | |
| CN | 101854891 A | 10/2010 | |
| CN | 101959519 A | 1/2011 | |
| CN | 103037802 A | 4/2013 | |
| CN | 103209733 A | 7/2013 | |
| CN | 103857431 A | 6/2014 | |
| CN | 204364577 U | 6/2015 | |
| EA | 006961 B1 | 6/2006 | |
| EP | 1188456 A1 | 3/2002 | |
| EP | 1568359 A1 | 8/2005 | |
| EP | 2193821 A1 | 6/2010 | |
| EP | 2307055 A2 | 4/2011 | |
| JP | 2001525826 A | 12/2001 | |
| JP | 2009183441 A | 8/2009 | |
| JP | 2009551298 A | 9/2009 | |
| JP | 2010234034 A | 10/2010 | |
| JP | 2013543418 A | 12/2013 | |
| JP | 5828535 B1 | 12/2015 | |
| KR | 20040096561 A | 11/2004 | |
| RU | 14351 U1 | 7/2000 | |
| RU | 2344767 C2 | 1/2009 | |
| RU | 2353393 C2 | 4/2009 | |
| RU | 2428956 C2 | 9/2011 | |
| WO | WO-1992008406 A1 | 5/1992 | |
| WO | WO-1992020389 A1 | 11/1992 | |
| WO | WO-1994001124 A1 | 1/1994 | |
| WO | WO-1994012217 A1 | 6/1994 | |
| WO | WO-1996009838 A1 | 4/1996 | |
| WO | WO-1998051348 A2 | 11/1998 | |
| WO | WO-2000007530 A2 | 2/2000 | |
| WO | WO-2000007565 A2 | 2/2000 | |
| WO | WO-0117589 A1 * | 3/2001 | ............. A61B 17/22 |
| WO | WO-2001041685 A2 | 6/2001 | |
| WO | WO-2002058769 A1 | 8/2002 | |
| WO | WO-2003002094 A2 | 1/2003 | |
| WO | WO-2003024507 A2 | 3/2003 | |
| WO | WO-2003039633 A2 | 5/2003 | |
| WO | WO-2004000389 A2 | 12/2003 | |
| WO | WO-2004105864 A1 | 12/2004 | |
| WO | WO-2005011741 A2 | 2/2005 | |
| WO | WO-2005032510 A1 | 4/2005 | |
| WO | WO-2005046641 A2 | 5/2005 | |
| WO | WO-2005069831 A2 | 8/2005 | |
| WO | WO-2005072701 A1 | 8/2005 | |
| WO | WO-2005074942 A1 | 8/2005 | |
| WO | WO-2005107845 A1 | 11/2005 | |
| WO | WO-2006004595 A2 | 1/2006 | |
| WO | WO-2006020714 A2 | 2/2006 | |
| WO | WO-2006042252 A2 | 4/2006 | |
| WO | WO-2006058189 A2 | 6/2006 | |
| WO | WO-2006128034 A1 | 11/2006 | |
| WO | WO-2006138719 A2 | 12/2006 | |
| WO | WO-2007069697 A1 | 6/2007 | |
| WO | WO-2007099406 A2 | 9/2007 | |
| WO | WO-2007100745 A2 | 9/2007 | |
| WO | WO-2007130105 A1 | 11/2007 | |
| WO | WO-2007131050 A2 | 11/2007 | |
| WO | WO-2007150018 A2 | 12/2007 | |
| WO | WO-2008082637 A1 | 7/2008 | |
| WO | WO-2009067325 A1 | 5/2009 | |

(56) References Cited

FOREIGN PATENT DOCUMENTS

| WO | WO-2009105534 A2 | 8/2009 |
|---|---|---|
| WO | WO-2009114521 A1 | 9/2009 |
| WO | WO-2010009034 A2 | 1/2010 |
| WO | WO-2010054660 A1 | 5/2010 |
| WO | WO-2010132751 A1 | 11/2010 |
| WO | WO-2011057065 A1 | 5/2011 |
| WO | WO-2011123722 A1 | 10/2011 |
| WO | WO-2011139713 A2 | 11/2011 |
| WO | WO-2012019136 A2 | 2/2012 |
| WO | WO-2012051575 A2 | 4/2012 |
| WO | WO-2012118498 A1 | 9/2012 |
| WO | WO-2012125869 A1 | 9/2012 |
| WO | WO-2012125872 A2 | 9/2012 |
| WO | WO-2012162459 A1 | 11/2012 |
| WO | WO-2013050236 A1 | 4/2013 |
| WO | WO-2013098166 A1 | 7/2013 |
| WO | WO-2013151904 A1 | 10/2013 |
| WO | WO-2014028285 A1 | 2/2014 |
| WO | WO-2014036009 A1 | 3/2014 |
| WO | WO-2014179698 A2 | 11/2014 |
| WO | WO-2014197317 A1 | 12/2014 |
| WO | WO-2015015467 A1 | 2/2015 |
| WO | WO-2015095772 A2 | 6/2015 |
| WO | WO-2015110660 A1 | 7/2015 |
| WO | WO-2015195842 A1 | 12/2015 |
| WO | WO-2015196085 A2 | 12/2015 |
| WO | WO-2016042162 A1 | 3/2016 |
| WO | WO-2016042163 A2 | 3/2016 |
| WO | WO-2017120600 A1 | 7/2017 |
| WO | WO-2017120601 A1 | 7/2017 |
| WO | WO-2017139375 A1 | 8/2017 |
| WO | WO-2017190142 A1 | 11/2017 |
| WO | WO-2017192565 A1 | 11/2017 |
| WO | WO-2022076938 A1 | 4/2022 |
| WO | WO-2024015652 A1 | 1/2024 |

OTHER PUBLICATIONS

Anthem, USA, "Medical Policy. Suprachoroidal Injection of a Pharmacologic Agent, " Last Review Date: Nov. 14, 2013, [online]. Retrieved from the Internet: URL: http://www.anthem.com/medicalpolicies/policies/mp_pw_b076412.htm. Retrieved from the Internet on: Oct. 24, 2014, American Medical Association, 3 pages.
Beer, P. J. et al., "Photographic Evidence of Vitreous Wicks After Intravitreal Injections," Retina Today, 2(2):24-39 (Mar. 2007).
Berglin, L. C. et al., "Tracing of Suprachoroidally Microneedle Injected Labled Drugs and Microbeads in Human, Pig and Rabbit Tissue Using Liquid Nitrogen Snap-Freeze Thaw and Lypholization Techniques," Invest Ophthalmol Vis Sci., 51:E-Abstract 5330 (2010), 2 pages.
Brown, D. M., "Aflibercept for Treatment of Diabetic Macular Edema," Retina Today, Jul./Aug. 2011, pp. 59-60.
Careforde Healthcare, B Braun Glass Loss-Of-Resistance Syringes # 332158-10cc Glass Loss-Of-Resistance Syringe, Luer Slip Metal Tip, 10/cs, (2014), 2 pages.
Careforde Inc., Careforde Healthcare, Chicago, IL, "B Braun Glass Loss-Of-Resistance Syringes # 332155-5cc Glass Loss-Of-Resistance Syringe, Luer Lock Metal Tip, 10/cs," [online]. Retrieved from the Internet: http://careforde.com/b-braun-glass-loss-of-resistance- syringes-332155-5cc-glass-loss-of-resistance-syringe-luer-lock-metal-tip-10-cs/. Retrieved from the Internet on: Oct. 16, 2014, (2014), 2 pages.
Careforde Inc., Careforde Healthcare, Chicago, IL, "B Braun Perifix Plastic Loss-Of-Resistance Syringes # 332152-8cc Plastic Luer Lock Loss-of-Resistance Syringe, 50/cs," [online]. Retrieved from the Internet: http://careforde.com/b-braun-perifix-plastic-loss-of-resistance-syringes-332152-8cc-plastic-luer-lock-loss-of-resistance-syringe-50-cs/. Retrieved from the Internet on: Oct. 16, 2014, (2014), 2 pages.
Choy, Y. B. et al., "Mucoadhesive microdiscs engineered for ophthalmic drug delivery: effect of particle geometry and fomulation on preocular residence time," Investigative Ophthalmology & Visual Science, 49:4808-4815 (2008).

Dinning, W. J., "Steroids and the eye-indications and complications," Postgraduate Medical Journal, vol. 52, 1976, pp. 634-638.
Doncaster and Bassetlaw Hospitals, Nhs Foundation Trust, Department of Ophthalmology, "Intravitreal injection of triamcinolone," Jul. 2010, [online]. Retrieved from the Internet: URL: http://www.dbh.nhs.uk/Library/Patient_Information_Leaflets/WPR32110%20IIT%20No%20crops.pdf, 2 pages.
Edwards, A. et al., "Fiber matrix model of sclera and corneal stroma for drug delivery to the eye," AIChE Journal, 44(1):214-225 (1998).
Einmahl, S. et al., "Evaluation of a novel biomaterial in the suprachoroidal space of the rabbit eye," Invest. Ophthalmol. Vis. Sci., 43(5):1533-1539 (2002).
Einmahl, S. et al., "Ocular biocompatibility of a poly(ortho ester) characterized by autocatalyzed degradation," J. Biomed. Mater. Res., 67(1):44-53 (2003).
"Epidural," Wikipedia [online], retrieved from the internet on Sep. 3, 2014, URL: http:/en.wikipedia.org/wiki/Epidural, 21 pages.
Examination Report for European Application No. 11776049.6, mailed Oct. 25, 2016, 4 pages.
Examination Report for Indian Application No. 201917009102, mailed Jul. 16, 2021, 6 pages.
Examination Report for Singapore Application No. 11201509051V, dated Feb. 1, 2017, 4 pages.
Examination Report No. 1 for Australian Application No. 2014259694, dated May 24, 2018, 2 pages.
Examination Report No. 1 for Australian Application No. 2015230874, dated Jul. 28, 2017, 11 pages.
Extended European Search Report for European Application No. 07751620.1, mailed Jan. 15, 2013, 10 pages.
Extended European Search Report for European Application No. 11777924.9, mailed Feb. 4, 2015, 7 pages.
Extended European Search Report for European Application No. 15810459.6, mailed Apr. 16, 2018, 11 pages.
Extended European Search Report for European Application No. 17750694.6, mailed Sep. 2, 2019, 6 pages.
Extended European Search Report for European Application No. 17880800.2, mailed Jun. 2, 2020, 13 pages.
Extended European Search Report for European Application No. 18176149.5, mailed Jan. 22, 2019, 11 pages.
Extended European Search Report for European Application No. 18176172.7, mailed Feb. 6, 2019, 11 pages.
Extended European Search Report for European Application No. 18199418.7, mailed Jul. 5, 2019, 9 pages.
Extended Search Report for European Application No. 13833318.2, dated Apr. 1, 2016, 7 pages.
Extended Search Report for European Application No. 14791646.4, dated Nov. 21, 2016, 6 pages.
Falkenstein, I. A. et al., "Comparison of visual acuity in macular degeneration patients measured with Snellen and Early Treatment Diabetic Retinopathy study charts," Ophthalmology 115(2):319-323 (Feb. 2008).
Feldkamp, L. A. et al., "Practical cone-beam algorithm," J. Opt. Soc. Am. A, 1(6):612-619 (1984).
First Examination Report for Indian Application No. 10270/DELNP/2015, mailed Apr. 5, 2021, 7 pages.
First Examination Report for Indian Application No. 3345/KOLNP/2008, dated May 21, 2015, 3 pages.
First Office Action for Chinese Application No. 200780014501.3, dated Mar. 11, 2010, 6 pages.
First Office Action for Chinese Application No. 201110093644.6, dated Mar. 26, 2012, 11 pages.
First Office Action for Chinese Application No. 201180060268.9, issued Oct. 10, 2014, 9 pages.
First Office Action for Chinese Application No. 201480025034.4, dated Apr. 24, 2018, 10 pages.
First Office Action for Chinese Application No. 201580044250.8, dated Apr. 24, 2018, 14 pages.
First Office Action for Chinese Application No. 201610805842.3, issued Jul. 21, 2017, 4 pages.
First Office Action for Chinese Application No. 201780062253.3, mailed Dec. 25, 2020, 22 pages.
First Office Action for Chinese Application No. 201910430078.X, issued Feb. 1, 2021, 8 pages.

(56) References Cited

OTHER PUBLICATIONS

Furrer, P. et al., "Ocular tolerance of preservatives and alternatives," European Journal of Pharmaceutics and Biopharmaceutics, 53(3):263-280 (2002).
Geroski, D. H. et al., "Drug delivery for posterior segment eye disease," Invest. Ophthalmol. Vis. Sci., 41(5):961-964 (2000).
Gilger, B. C. et al., "Treatment of acute posterior uveitis in a porcine model by injection of triamcinolone acetonide into the suprachoroidal space using microneedles," Investigative Ophthalmology & Visual Science, 54(4):2483-2492 (2013).
Gilger, et al., "A Novel Bioerodible Deep Scleral Lamellar Cyclosporine Implant for Uveitis," Invest Ophthalmol Vis Sci, vol. 47, Issue 6, 2006, pp. 2596-2605.
Haller, J. A. et al., "Evaluation of the safety and performance of an applicator for a novel intravitreal dexamethasone drug delivery system for the treatment of macular edema," Retina, 29(1):46-51 (2009).
Haller, J. A., "Intraocular Steroids in the Office. New formulations offer preservative-free triamcinolone without relying on compounding pharmacies," Retinal Physician [online]. Retrieved from the Internet: URL: https://www.retinalphysician.com/supplements/2009/february-2009/special-edition/intraocular-steroids-in-the-office, Feb. 1, 2009, 4 pages.
Hanekamp, S. et al., "Inhibition of Corneal and Retinal Angiogenesis by Organic Integrin Antagonists After Intrascleral or Intravitreal Drug Delivery," Invest Ophthalmol Vis. Sci., 43: E-Abstract 3710, ARVO (2002), 2 pages.
Heller, J., Ocular delivery using poly(ortho esters), Adv. Drug. Deliv. Rev., 57(14):2053-2062 (2005).
Hogan et al., Chapter Eight, Choroid, In Histology of the Human Eye, 9 pages (1971).
HomeCEU, "How Does Iontophoresis Work?", [Online], Retrieved from the Internet: https://www.homeceuconnection.com/blog/how-does-iontophoresis-work/, 2018, 5 pages.
International Search Report and Written Opinion for International Application No. PCT/US2007/004874, mailed Jun. 4, 2008, 6 pages.
International Search Report and Written Opinion for International Application No. PCT/US2007/068055, mailed Nov. 7, 2007, 13 pages.
International Search Report and Written Opinion for International Application No. PCT/US2011/033987, mailed Feb. 14, 2012, 7 pages.
International Search Report and Written Opinion for International Application No. PCT/US2011/056433, mailed Apr. 25, 2012, 17 pages.
International Search Report and Written Opinion for International Application No. PCT/US2013/056863, mailed Nov. 26, 2013, 8 pages.
International Search Report and Written Opinion for International Application No. PCT/US2014/036590, mailed Dec. 10, 2014, 10 pages.
International Search Report and Written Opinion for International Application No. PCT/US2014/040254, mailed Oct. 31, 2014, 9 pages.
International Search Report and Written Opinion for International Application No. PCT/US2015/036299, mailed Nov. 10, 2015, 11 pages.
International Search Report and Written Opinion for International Application No. PCT/US2015/036715, mailed Jan. 19, 2016, 9 pages.
International Search Report and Written Opinion for International Application No. PCT/US2017/017014, mailed Apr. 27, 2017, 13 pages.
International Search Report and Written Opinion for International Application No. PCT/US2017/030439, mailed Aug. 1, 2017, 12 pages.
International Search Report and Written Opinion for International Application No. PCT/US2017/030609, mailed Oct. 6, 2017, 12 pages.
International Search Report and Written Opinion for International Application No. PCT/US2017/046553, mailed Dec. 13, 2017, 14 pages.
International Search Report and Written Opinion for International Application No. PCT/US2017/065796, mailed Apr. 12, 2018, mailed Apr. 12, 2018, 9 pages.
Invitation pursuant to Article 94(3) and Rule 71(1) for European Application No. 07751620.1, mailed Feb. 29, 2016, 3 pages.
Jain, A., "Pseudo loss of resistance in epidural space localization: A complication of subcutaneous emphysema or simply a faulty technique," Saudi J. Anaseth, 5(1): 108-109 (2011) (Abstract).
Jiang, et al., "Intrascleral Drug Delivery to the Eye Using Hollow Microneedles", Pharmaceutical Research, vol. 26, Issue 2, 2009, pp. 395-403.
Jiang, J. et al., "Coated Microneedles for Drug Delivery to the Eye," Investigative Ophthalmology & Visual Science, 48(9):4038-4043 (2007).
Jiang, J. et al., "Measurement and Prediction of Lateral Diffusion within Human Sclera," Investigative Ophthalmology & Visual Science, 47(7):3011-3016 (2006).
Kadam, R. S. et al., "Suprachoroidal delivery in a rabbit ex vivo eye model: influence of drug properties, regional differences in delivery, and comparison with intravitreal and intracameral routes," Molecular Vision, 19:1198-1210 (May 2013).
Karim, R. et al., "Interventions for the treatment of uveitic macular edema: a systematic review and meta-analysis," Clinical Ophthalmology, 7:1109-1144 (2013).
Lee et al., "Thixotropic property in pharmaceutical formulations," Journal of Controlled Release (2009) 136:88-98.
Lee, S-B et al., "Drug delivery through the sclera: effects of thickness, hydration and sustained release systems," Experimental Eye Research, 78:599-607 (2004).
Lindfield, D. et al., "Suprachoroidal Devices in Glaucoma. The Past, Present, and Future of Surgery for Suprachoroidal Drainage," Cataract & Refractive Surgery Today Europe, [online], Oct. 2013, Retrieved from the Internet: URL: http://bmctoday.net/crstodayeurope/2013/10/article.asp?f=suprachoroidal-devices-in-glaucoma. Retrieved from the Internet on: Oct. 24, 2014, Bryn Mawr Communications LLC, Wayne, PA, USA, 3 pages.
Loewen, N., "The suprachoroidal space in glaucoma surgery," Jul. 2012, 4 pages.
Maurice, D., "Review: Practical Issues in Intravitreal Drug Delivery," J. Ocul. Pharmacol. Ther., 17(4):393-401 (2001).
Mcallister, et al., "Microfabricated needles for transdermal delivery of macromolecules and nanoparticles: rabrication methods and transport studies", Proceedings of the Natural Academy of Science, vol. 100, Issue 24, 2003, pp. 13755-13760.
Norman, D., Epidural analgesia using loss of resistance with air versus saline: Does it make a difference? Should we reevaluate our practice?, AANA Journal, 71(6):449-453 (Dec. 2003).
Notice of Reasons for Rejection for Japanese 2018-557826, mailed Mar. 29, 2021, 13 pages.
Notice of Reasons for Rejection for Japanese Application No. 2016-512068, mailed Mar. 26, 2018, 4 pages.
Notice of Reasons for Rejection for Japanese Application No. 2016-574090, mailed Mar. 4, 2019, 18 pages.
Notice of Reasons for Rejection for Japanese Application No. 2018-142345, mailed Jun. 6, 2019, 6 pages.
Office Action for Brazilian Application No. 112012027416-3, mailed Nov. 14, 2021, 4 pages.
Office Action for Brazilian Application No. 112013009205-0, dated Sep. 17, 2019, 4 pages.
Office Action for Brazilian Application No. PI 0708133-2, dated Feb. 26, 2019, 11 pages.
Office Action for Canadian Application No. 162010, dated Aug. 25, 2015, 1 page.
Office Action for Canadian Application No. 2797258, dated Nov. 21, 2016, 3 pages.
Office Action for Canadian Application No. 2,882,184, dated Aug. 18, 2020, 3 pages.
Office Action for Canadian Application No. 2,882,184, dated Jan. 24, 2020, 6 pages.

(56) References Cited

OTHER PUBLICATIONS

Office Action for Canadian Application No. 2,882,184, dated May 1, 2019, 3 pages.
Office Action for Canadian Application No. 2,911,290, dated Jun. 18, 2020, 5 pages.
Office Action for Chinese Application No. 201510144330.2, issued Apr. 5, 2016, 17 pages.
Office Action for Eurasian Application No. 201592109, mailed Apr. 1, 2016, 4 pages.
Office Action for Eurasian Application No. 201592109, mailed Jan. 31, 2018, 2 pages.
Office Action for European Application No. 07751620.1, dated Dec. 11, 2014, 5 pages.
Office Action for European Application No. 07751620.1, dated Sep. 13, 2013, 7 pages.
Office Action for European Application No. 11777924.9, mailed Oct. 1, 2019, 5 pages.
Office Action for European Application No. 13833318.2, dated Apr. 20, 2021, 4 pages.
Office Action for European Application No. 13833318.2, dated Aug. 26, 2020, 5 pages.
Office Action for European Application No. 13853777.4, mailed Apr. 10, 2018, 8 pages.
Office Action for European Application No. 14791646.4, dated Dec. 4, 2017, 5 pages.
Office Action for European Application No. 14791646.4, dated Feb. 11, 2020, 5 pages.
Office Action for European Application No. 14791646.4, dated Sep. 17, 2018, 5 pages.
Office Action for European Application No. 14808034.4, mailed Nov. 8, 2017, 4 pages.
Office Action for European Application No. 17755007.6, mailed Jun. 25, 2021, 6 pages.
Office Action for European Application No. 18176172.7, mailed Feb. 7, 2020, 4 pages.
Office Action for European Application No. 18199418.7, mailed Nov. 10, 2020, 5 pages.
Office Action for Indian Application No. 10099/DELNP/2012, mailed Jul. 2, 2019, 5 pages.
Office Action for Israeli Application No. 242395, dated Aug. 10, 2020, 12 pages.
Office Action for Israeli Application No. 242395, dated May 7, 2019, 7 pages.
Office Action for Japanese Application No. 2008-556462, dated Jul. 24, 2012, 15 pages.
Office Action for Japanese Application No. 2013-534049, mailed Sep. 1, 2015, 11 pages.
Office Action for Japanese Application No. 2016-068174, mailed Mar. 1, 2017, 8 pages.
Office Action for Korean Application No. 10-2015-7034411, dated Nov. 16, 2020, 8 pages.
Office Action for Mexican Application No. MX/a/2015/015282, dated May 15, 2019, 8 pages.
Office Action for Mexican Application No. MX/a/2015/015282, dated Oct. 26, 2018, 4 pages.
Office Action for New Zealand Application No. 714172, dated Dec. 12, 2018, 3 pages.
Office Action for New Zealand Application No. 714172, dated Feb. 1, 2018, 4 pages.
Office Action for New Zealand Application No. 714172, dated Jul. 24, 2018, 4 pages.
Office Action for Russian Application No. 2012147341, dated Feb. 26, 2015, 8 pages.
Office Action for Russian Application No. 2017101660, dated Mar. 5, 2019, 7 pages.
Office Action for Singapore Application No. 200805936-2, dated Oct. 15, 2012, 7 pages.
Office Action for U.S. Appl. No. 11/709,941, mailed Apr. 12, 2016, 25 pages.
Office Action for U.S. Appl. No. 11/709,941, mailed Dec. 14, 2018, 17 pages.
Office Action for U.S. Appl. No. 11/709,941, mailed Dec. 27, 2016, 28 pages.
Office Action for U.S. Appl. No. 11/709,941, mailed Feb. 11, 2015, 14 pages.
Office Action for U.S. Appl. No. 11/709,941, mailed Jan. 16, 2018, 32 pages.
Office Action for U.S. Appl. No. 11/709,941, mailed Jun. 24, 2014, 11 pages.
Office Action for U.S. Appl. No. 11/709,941, mailed Mar. 23, 2011, 9 pages.
Office Action for U.S. Appl. No. 11/709,941, mailed Oct. 27, 2011, 8 pages.
Office Action for U.S. Appl. No. 11/743,535, mailed Aug. 19, 2010, 7 pages.
Office Action for U.S. Appl. No. 11/743,535, mailed Dec. 29, 2009, 6 pages.
Office Action for U.S. Appl. No. 12/767,768, mailed Jun. 10, 2011, 5 pages.
Office Action for U.S. Appl. No. 13/273,775, mailed Feb. 12, 2015, 13 pages.
Office Action for U.S. Appl. No. 13/273,775, mailed Jul. 3, 2014, 12 pages.
Office Action for U.S. Appl. No. 13/447,246, mailed Oct. 28, 2013, 5 pages.
Office Action for U.S. Appl. No. 13/453,407, mailed Mar. 20, 2013, 5 pages.
Office Action for U.S. Appl. No. 13/842,218, mailed Jul. 5, 2016, 11 pages.
Office Action for U.S. Appl. No. 13/842,288, mailed Oct. 6, 2015, 10 pages.
Office Action for U.S. Appl. No. 14/136,657, mailed Dec. 16, 2016, 7 pages.
Office Action for U.S. Appl. No. 14/268,687, mailed May 19, 2016, 6 pages.
Office Action for U.S. Appl. No. 14/424,685, mailed Dec. 12, 2016, 15 pages.
Office Action for U.S. Appl. No. 14/424,685, mailed Jun. 10, 2016, 10 pages.
Office Action for U.S. Appl. No. 14/441,151, mailed Sep. 9, 2016, 18 pages.
Office Action for U.S. Appl. No. 14/523,243, mailed Feb. 27, 2015, 14 pages.
Office Action for U.S. Appl. No. 14/821,310, mailed Jul. 14, 2017, 11 pages.
Office Action for U.S. Appl. No. 14/894,161, mailed Apr. 6, 2018, 19 pages.
Office Action for U.S. Appl. No. 14/894,161, mailed Dec. 27, 2016, 17 pages.
Office Action for U.S. Appl. No. 14/894,161, mailed Sep. 20, 2017, 21 pages.
Office Action for U.S. Appl. No. 15/001,610, mailed Sep. 8, 2016, 12 pages.
Office Action for U.S. Appl. No. 15/086,485, mailed Jul. 28, 2016, 9 pages.
Office Action for U.S. Appl. No. 15/319,045, mailed Jul. 13, 2018, 13 pages.
Office Action for U.S. Appl. No. 15/383,582, mailed May 5, 2017, 10 pages.
Office Action for U.S. Appl. No. 15/398,538, mailed Apr. 16, 2019, 8 pages.
Office Action for U.S. Appl. No. 15/398,538, mailed Jul. 20, 2018, 12 pages.
Office Action for U.S. Appl. No. 15/427,823, mailed Apr. 20, 2017, 8 pages.
Office Action for U.S. Appl. No. 15/427,823, mailed Jul. 20, 2018, 11 pages.
Office Action for U.S. Appl. No. 15/427,823, mailed Sep. 27, 2017, 7 pages.
Office Action for U.S. Appl. No. 15/619,065, mailed Jan. 28, 2020, 24 pages.

(56) References Cited

OTHER PUBLICATIONS

Office Action for U.S. Appl. No. 15/619,065, mailed Jun. 11, 2021, 18 pages.
Office Action for U.S. Appl. No. 15/619,065, mailed Jun. 13, 2019, 30 pages.
Office Action for U.S. Appl. No. 15/619,065, mailed Nov. 27, 2020, 23 pages.
Office Action for U.S. Appl. No. 15/675,035, mailed Jun. 11, 2020, 14 pages.
Office Action for U.S. Appl. No. 15/708,779, mailed Jul. 15, 2019, 8 pages.
Office Action for U.S. Appl. No. 15/872,206, mailed May 1, 2020, 8 pages.
Office Action for U.S. Appl. No. 15/872,206, mailed Oct. 19, 2020, 9 pages.
Office Action for U.S. Appl. No. 15/946,838, mailed Jun. 27, 2019, 7 pages.
Office Action for U.S. Appl. No. 16/178,162, mailed Jun. 10, 2020, 18 pages.
Office Action for U.S. Appl. No. 16/178,162, mailed May 11, 2021, 48 pages.
Office Action for U.S. Appl. No. 16/381,213, mailed May 31, 2019, 7 pages.
Office Action for U.S. Appl. No. 16/591,067, mailed Nov. 18, 2019, 7 pages.
Office Action for U.S. Appl. No. 16/826,443, mailed Jun. 1, 2020, 6 pages.
Office Action for U.S. Appl. No. 17/217,455, mailed Jun. 23, 2021, 13 pages.
Office Action for U.S. Appl. No. 17/217,455, mailed Oct. 21, 2021, 15 pages.
Olsen, T., "Drug Delivery to the Suprachoroidal Space Shows Promise," Retina Today, pp. 36-39 (Mar./Apr. 2007).
Olsen, T. W. et al., "Cannulation of the Suprachoroidal Space: A Novel Drug Delivery Methodology to the Posterior Segment," American J. Opthamology, 142(5):777-787 (2006).
Ozkiris, A., "Intravitreal Triamcinolone Acetonide Injection for the Treatment of Posterior Uveitis," Ocular Immunology and Inflammation, vol. 14, Issue 4, pp. 233-238 (May 2006), Published online: Jul. 8, 2009 (Abstract).
Partial European Search Report for European Application No. 18176172.7, mailed Oct. 30, 2018, 13 pages.
Partial Supplementary European Search Report for European Application No. 15810459.6, mailed Dec. 22, 2017, 13 pages.
Patel, S. et al., "Drug Binding to Sclera," Invest Ophthalmol Vis Sci., 50:E-Abstract 5968 (2009), 2 pages.
Patel, S. et al., "Suprachoroidal Drug Delivery Using Microneedles," Invest. Ophthalmol. Vis. Sci., 49:E-Abstract 5006 (2008), 2 pages.
Patel, S. R. et al., "Intraocular Pharmacokinetics of Suprachoroidal Drug Delivery Administered Using Hollow Microneedles," Invest Ophthalmol Vis Sci., 51:E-Abstract 3796 (2010), 2 pages.
Patel, S. R. et al., "Targeted administration into the suprachoroidal space using a microneedle for drug delivery to the posterior segment of the eye," Investigative Ophthalmology & Visual Science, 53(8):4433-4441 (Jul. 2012).
Penkov, M. A. et al., "A ten-year experience with usage of the method of supra-choroidal administration of medicinal substances," Oftalmol. Zh., 35(5):281-285 (1980) (Translated from Russian).
Prausnitz, M. R. et al., "Measurement and prediction of transient transport across sclera for drug delivery to the eye," Industrial and Engineering Chemistry Research, 37(8):2903-2907 (1998).
Prausnitz, M. R., "Microneedles for Ocular Drug Delivery," Review of Olsen, T., Drug Delivery to the Suprachoroidal Space Shows Promise, Retina Today, Mar./Apr. 2007, p. 39.
Prausnitz, "Microneedles for transdermal drug delivery", Advanced Drug Delivery Reviews, vol. 56, 2004, pp. 581-587.
Preliminary Office Action for Brazilian Application No. 112012027416-3, mailed Jul. 11, 2021, 2 pages.
Preliminary Office Action for Brazilian Application No. 112015027762-4, dated Jan. 17, 2020, 6 pages.
Preliminary Rejection for Korean Application No. 10-2021-7023167, dated Aug. 17, 2021, 7 pages.
Rowe-Rendleman, C. L. et al., "Prophylactic Intra-Scleral Injection of Steroid Compounds in Rabbit Model of Retinal Neovascularization," Invest Ophthalmol Vis. Sci., 43:E-Abstract 3872, ARVO (2002), 2 pages.
Saberski, L. R. et al., "Identification of the epidural space: Is loss of resistance to air a safe technique? A review of the complications related to the use of air," Regional Anesthesia, 22(1):3-15 (1997).
Sallam, A. et al., "Repeat intravitreal triamcinolone acetonide injections in uveitic macular oedema," Acta Ophthalmologica, 90(4):e323-e325 (2012).
Scott, I. U. et al., "Baseline characteristics and response to treatment of participants with hemiretinal compared with branch retinal or central retinal vein occlusion in the standard care vs. corticosteroid for retinal vein occlusion (SCORE)," Arch. Ophthalmol., 130(12):1517-1524 (Dec. 2012).
Search Report and Written Opinion for Singapore Application No. 11201503637S, mailed Jun. 23, 2016, 9 pages.
Search Report and Written Opinion for Singapore Application No. 11201509051V, dated Nov. 2, 2016, 6 pages.
Search Report and Written Opinion for Singapore Application No. 200805936-2, dated Jun. 8, 2010, 13 pages.
Second Office Action for Chinese Application No. 200780014501.3, dated Aug. 26, 2010, 10 pages.
Second Office Action for Chinese Application No. 201110093644.6, dated Sep. 7, 2012, 8 pages.
Second Office Action for Chinese Application No. 201180060268.9, issued Jun. 18, 2015, 4 pages.
Second Office Action for Chinese Application No. 201510144330.2, issued Dec. 20, 2016, 13 pages.
Second Office Action for Chinese Application No. 201910430078.X, issued Aug. 18, 2021, 5 pages.
Shuler, R. K. et al., "Scleral Permeability of a Small, Single-Stranded Oligonucleotide," Journal of Ocular Pharmacology and Therapeutics, 20(2): 159-168 (2004) (Abstract).
Summons to Attend Oral Proceedings Pursuant to Rule 115(1) EPC for European Application No. 07751620.1, mailed Jun. 13, 2017, 8 pages.
Supplementary European Search Report for European Application No. 14808034.4, mailed Jan. 23, 2017, 7 pages.
Supplementary Partial European Search Report for European Application No. 13853777.4, mailed Jul. 4, 2016, 6 pages.
Supplementary Search Report for Singapore Application No. 200805936-2, dated May 26, 2011, 8 pages.
Supplementary Search Report for Singapore Application No. 200805936-2, dated May 6, 2011, 8 pages.
Third Office Action for Chinese Application No. 201110093644.6, dated Dec. 14, 2012, 3 pages.
Third Office Action for Chinese Application No. 201180060268.9, issued Feb. 5, 2016, 6 pages.
Third Office Action for Chinese Application No. 201510144330.2, issued Jun. 28, 2017, 3 pages.
Wang, P. M. et al., "Minimally Invasive Extraction of Dermal Interstitial Fluid for Glucose Monitoring Using Microneedles," Diabetes Technology & Therapeutics, 7(1):131-141 (2005).
You, X. D. et al., "Chitosan drug delivery system implanting into suprachoroidal space for perforating ocular injury in rabbits," International Journal of Ophthalmology, 5(1):74-76 (2005) [English Abstract].
Al-Shaikh, B. et al., 2007, "Essentials of Anaesthetic Equipment," Edinburgh: Churchill Livingstone, 3rd Edition, 7 pages.
Amaratunga, A. et al., "Inhibition of Kinesin Synthesis and Rapid Anterograde Axonal Transport in Vivo by an Antisense Oligonucleotide," The Journal of Biological Chemistry, Aug. 1993, vol. 268, No. 23, pp. 17427-17430.
Bunnelle, E., "Syringe Diameters," [online] 2005. Cchem.berkeley.edu. Available at: http://www.cchem.berkeley.edu/rsgrp/Syringediameters.pdf [Accessed Mar. 11, 2022], 3 pages.
Dogliotti, A. M., "Research and Clinical Observations on Spinal Anesthesia: With Special Reference to the Peridural Technique," Current Researches in Anesthesia & Analgesia, Mar.-Apr. 1933, vol. 12, Issue 2, pp. 59-65.

(56) References Cited

OTHER PUBLICATIONS

Final Office Action for U.S. Appl. No. 17/711,495 dated Jan. 17, 2023, 36 pages.
Final Rejection Office Action for U.S. Appl. No. 16/178,162 mailed on May 16, 2022, 55 pages.
Habib, A. S et al., "The AutoDetect Syringe Versus the Glass Syringe for the Loss of Resistance Technique in Parturients," Duke University Medical Center, Durham, North Carolina, Oct. 2007, 2 pages.
Harvardapparatus.com. 2011. Syringe Selection Guide. [online] Available at: https://www.harvardapparatus.com/media/harvard/pdf/Syringe%20Selection%20Guide.pdf , [Accessed Mar. 11, 2022], 4 pages.
International Preliminary Report on Patentability for International Application No. PCT/US2021/054395 dated Apr. 20, 2023, 11 pages.
International Search Report and Written Opinion for International Application No. PCT/US2021/054395, mailed Mar. 14, 2022, 16 pages.
Invitation to Pay Additional Fees for International Application No. PCT/US2021/054395, mailed Dec. 8, 2021, 4 pages.
Kim, S. H. et al., "Assessment of Subconjunctival and Intrascleral Drug Delivery to the Posterior Segment Using Dynamic Contrast-Enhanced Magnetic Resonance Imaging," Invest Ophthalmol Vis Sci, vol. 48, No. 2, Feb. 2007, pp. 808-814.
Mansoor, S. et al., "Pharmacokinetics and Biodistribution of Triamcinolone Acetonide Following Suprachoroidal Injection into the Rabbit Eye In Vivo Using a Microneedle," Investigative Ophthalmology & Visual Science, ARVO Annual Meeting Abstract, Apr. 2011, vol. 52, 6585, 2 pages.
Non-Final Office Action for U.S. Appl. No. 17/711,495 mailed on Sep. 7, 2022, 26 pages.
Non-Final Office Action for U.S. Appl. No. 17/711,495, filed Aug. 2, 2022, 15 pages.
Notice of Opposition for European Application No. 14791646.4, dated Mar. 29, 2022, 38 pages.
Office Action for Brazilian Application No. 112015027762-4, dated Jan. 28, 2022, 19 pages.
Office Action for Brazillian Application No. BR1120150277624 dated Mar. 22, 2023, 3 pages.
Office Action for Chinese application No. CN201910430078, mailed on Jul. 7, 2022, 7 pages.
Office Action for European Application No. 17880800.2, mailed Apr. 14, 2022, 10 pages.
Office Action for European Application No. 18199418.7, mailed May 18, 2022, 5 pages.
Office Action for European Application No. EP20180199418 dated Apr. 13, 2023, 4 pages.
Office Action for Israel application No. 1286808, mailed on Oct. 20, 2022, 7 pages.
Office Action for Israeli Application No. 264764, dated Feb. 28, 2022, 7 pages.
Patel, S. R. et al., "Suprachoroidal drug delivery to the back of the eye using hollow microneedles," Pharmaceutical Research, Sep. 21, 2010, Vo. 28, No. 1, pp. 166-176.
Patel, S. R., "Suprachoroidal drug delivery to the eye using hollow microneedles," Dissertation, Georgia Institute of Technology, May 2011, 177 pages.
Stein, L. et al., "Clinical gene therapy for the treatment of RPE65-associated Leber congenital amaurosis," Expert Opin. Biol. Ther., Mar. 2011, vol. 11, No. 3, pp. 429-439.
Syringepump.com. 2012. NE-300 Just Infusion ™ Syringe Pump. [online] Available at: https://www.syringepump.com/download/NE-300Brochure.pdf [Accessed Mar. 11, 2022], 5 pages.
Third Office Action for Chinese Application No. 201910430078.X, issued Mar. 29, 2022, 12 pages.
Final Office Action for U.S. Appl. No. 17/062,096, mailed Oct. 25, 2023, 9 pages.
International Search Report and Written Opinion for Intl. Application No. PCT/US2023/066324, mailed Aug. 7, 2023, 11 pages.
Non-Final Office Action for U.S. Appl. No. 16/440,108, mailed Dec. 4, 2023, 14 pages.
Non-Final Office Action for U.S. Appl. No. 17/208,235 mailed Aug. 21, 2023, 20 pages.
Non-Final Office Action for U.S. Appl. No. 18/365,024, mailed Oct. 12, 2023, 10 pages.
Office Action for Canadian Application No. CA20173062845, mailed Jul. 21, 2023, 4 pages.
Office Action for Canadian Application No. CA20173072847, mailed Sep. 29, 2023, 4 pages.
Office Action for Mexican Application No. MX20180013502, mailed Aug. 4, 2023, 3 pages.
Office Action for European Application No. EP18199418.7, mailed May 29, 2024, 5 pages.

\* cited by examiner

DEVICE FOR OCULAR ACCESS

CROSS-REFERENCE TO RELATED APPLICATIONS

This application is a continuation of U.S. patent application Ser. No. 17/208,235, entitled "Device for Ocular Access," filed Mar. 22, 2021, which is a continuation of U.S. patent application Ser. No. 15/872,206, entitled "Device for Ocular Access," filed Jan. 16, 2018, now U.S. Pat. No. 10,952,894, which is a continuation of U.S. patent application Ser. No. 14/821,310, entitled "Device for Ocular Access," filed Aug. 7, 2015, now abandoned, which is a continuation of U.S. patent application Ser. No. 13/273,775, entitled "Device for Ocular Access," filed Oct. 14, 2011, now abandoned, which claims priority to U.S. Provisional Application Ser. No. 61/393,741, entitled "Device for Ocular Access," filed Oct. 15, 2010, the entirety of each of which is incorporated herein by reference.

BACKGROUND OF INVENTION

The suprachoroidal space is a potential space in the eye that is located between the choroid, which is the middle layer or vascular tunic of the eye, and the sclera, the outer (white) layer of the eye. The suprachoroidal space extends from the anterior portion of the eye near the ciliary body to the posterior end of the eye adjacent to the optic nerve. Normally the suprachoroidal space is not evident due to the close apposition of the choroid to the sclera from the intraocular pressure of the eye. Since there is no substantial attachment of the choroid to the sclera, the tissues can separate to form the suprachoroidal space when fluid accumulation or other conditions occur. The suprachoroidal space provides a potential route of access from the anterior region of the eye to the posterior region for the delivery of treatments for diseases of the eye. Standard surgical access to the suprachoroidal space is achieved through incisions in the conjunctiva and the sclera, and is primarily performed in an operating room. Surgical access is useful in draining choroidal effusions or hemorrhage, and in placing microcatheters and cannulas into the suprachoroidal space for delivery of agents to the back of the eye. Treatments for diseases such as age-related macular degeneration, macular edema, diabetic retinopathy and uveitis may be treated by the appropriate active agent administered in the suprachoroidal space.

The sub-retinal space is a potential space in the eye that is located between the sensory retina and the choroid. The sub-retinal space lies under all portions of the retina, from the macular region near the posterior pole to the ora serrata, the anterior border of the retina. Normally the sub-retinal space is not evident as the retina needs to be apposed to the underlying choroid for normal health and function. In some disease states or as a result of trauma, a retinal detachment may occur, forming a fluid filled region in the sub-retinal space. Such spaces normally require treatment to reattach the retina before retinal function is irreversibly lost. However, it has been found that some treatments such as gene therapy or cell therapeutics may be applied to the sub-retinal space to provide maximum exposure to the retina. In a normally functioning retina, small injections in the sub-retinal space create a small area of retinal detachment which resolves in a short period of time, allowing direct treatment of the retina.

The sub-retinal space may be accessed ab-interno by piercing a small gauge needle through the retina. This procedure involves penetration of the intraocular space of the eye and forming a small retinotomy by the needle. A therapeutic agent injected into the sub-retinal space may flow out through the retinotomy into the vitreous cavity causing exposure of the therapeutic to the lens, ciliary body and cornea as it exits through the anterior aqueous outflow pathway.

It is desired to have a method whereby the suprachoroidal space or the sub-retinal space may be accessed in a minimally invasive method via an ab-externo transconjunctival approach. Such a method would provide a method to limit, guide or guard the penetration of a needle device into the suprachoroidal space or sub-retinal space to prevent further penetration. The present invention provides an apparatus to allow minimally invasive, transconjunctival access to the suprachoroidal space or sub-retinal space in the eye for the delivery of therapeutic or diagnostic materials.

SUMMARY OF THE INVENTION

The present invention provides a device comprising an elongated body having a distal end and proximal end, said ends in communication through an internal pathway within the body wherein:
the distal end is configured with a sharp edge or point to penetrate into ocular tissues of the outer shell of the eye,
a moveable guarding element disposed in a first configuration to shield the ocular tissues from the sharp edge or point, and adapted to apply a distally directed force to the tissues at the distal end of the device to displace tissue away from the distal end of the device upon entry into the suprachoroidal space or subretinal space in an eye with the distal end; wherein the guarding element is moveable to a second configuration to expose said sharp edge or point to said tissues for penetration into the tissues,
and an access port to deliver materials and substances through the pathway in the elongated body after deployment of the guarding element within the suprachoroidal space or subretinal space.

In some embodiments the guarding element is attached to a spring or compressible element that upon compression thereof provides a distally directed force on the guarding element.

In some embodiments the guarding element comprises a flowable material selected from a fluid or gas that is directed to flow out of the distal end of the device to provide a distally directed force.

In some embodiments the device further comprises a sealing element attached at the distal end of the elongated body adapted to reduce or prevent leakage of fluid or gas through a tissue tract created by the device.

In some embodiments the device accommodates a spring to apply a distal force on the sealing element to provide a sealing force of the element against the eye tissue.

In some embodiments the device comprises a reservoir at the proximal end for receiving a material to be delivered at the target space and the sealing element is in mechanical communication with an activating element for releasing the material from the reservoir.

In some embodiments the device comprises an associated sealing element adapted for retention on the surface of the eye to receive the distal end of the device to locate and stabilize the device during penetration into the eye.

The invention further provides a device for placement in the sclera of an eye, comprising a body having a proximal end adapted for location at or near the scleral surface and a distal end adapted for location within the suprachoroidal or subretinal space, where the device comprises a lumen and a mechanical stop at the proximal end for retaining the proximal end at or near the scleral surface.

Methods of using the devices of the invention to access the suprachoroidal or subretinal spaces of the eye are also provided.

DESCRIPTION OF EMBODIMENTS OF THE INVENTION

Figure 1:
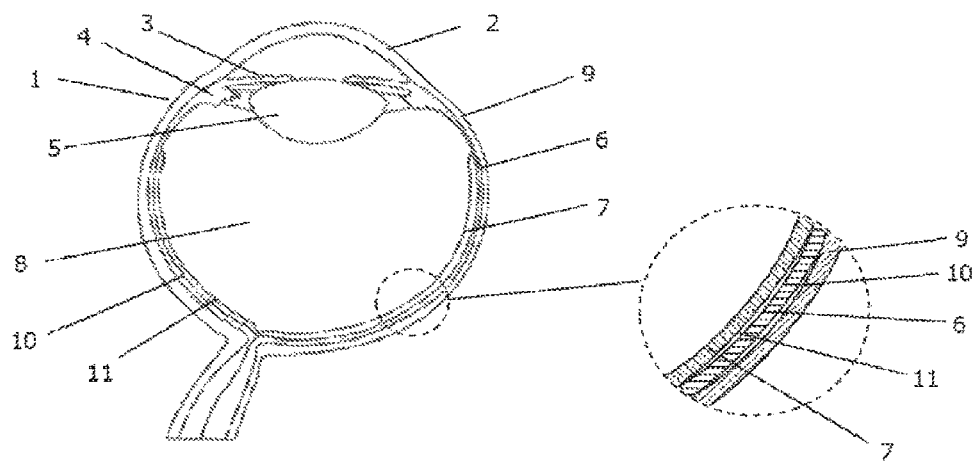
FIG. 1 is a schematic cross-section of the eye with a detail view of the layers of the eye.

The present invention provides methods and devices to access the suprachoroidal space or sub-retinal space in an eye via a minimally invasive transconjunctival approach to eliminate the need for dissection and subsequent suture closure of the dissection. The devices may also be used after a partial dissection, for example after dissection of the outer scleral layer of the eye, whereby the device is used within the dissection to access the suprachoroidal space or the sub-retinal space. Specifically, the invention provides devices that advantageously may be used in an operating room- or treatment room based setting, to allow for the delivery of substances to the suprachoroidal space or sub-retinal space. Of particular utility is the use of the device to deliver drugs or drug containing materials which provide sustained availability of the drug to the eye. Drugs injected with the device to the suprachoroidal space are useful for treating the choroid and through the vasculature of the choroid, the inner tissues of the eye. Drugs injected with the device to the sub-retinal space are useful for treating the retinal pigment epithelia and the sensory retina. Some examples include polymer drug release materials in the form of injectable filaments or microspheres, or drugs with limited solubility that would provide slow release of drug to the eye. Limited solubility steroids such as triamcinolone acetonide or loteprednol etabonate are steroids which may be injected into the suprachoroidal in a suspension formulation.

The devices comprise an elongated body with a distal and a proximal ends, where the device is held by the operator at the proximal end. The distal end may be configured to penetrate the conjunctiva and the sclera, but not the choroid to access the suprachoroidal space. Alternatively, the distal end may be configured to penetrate the conjunctiva, sclera, and the choroid but not the retina to access the sub-retinal space. The device may contain substances to be delivered through the distal end once placed into the suprachoroidal or sub-retinal spaces. Alternatively, the proximal end may be configured to receive apparatus for the delivery of substances such as a syringe. The devices may also be adapted to place a thin-walled sleeve, as a port or introducer, into the suprachoroidal space or sub-retinal space to allow for subsequent placement and advancement of cannulae or catheters.

In certain preferred embodiments, the device is adapted to limit penetration depth and/or to safely displace the choroid or retina away from the overlying tissue, thereby allowing the distal tip to penetrate into the suprachoroidal space or sub-retinal space, but preventing the distal tip from penetrating or causing damage to the choroid or retina itself. Displacement-limiting or guarding elements may be provided through mechanical or fluidic mechanisms to provide a forward (distally) directed force to the tissues in the eye at the distal tip of the device. The guarding elements may be self-activated by the device or manually activated by the surgeon at the appropriate time. In conjunction with a fluidic mechanism acting as a guarding element, the device may incorporate a sealing element directed at the site of penetration of the eye to prevent leakage of the fluidic element that might cause undesired reduction of the degree of intended displacement of the underlying choroid or retina.

As shown in FIG. 1, the eye 1 is a globe with two main sections, the anterior segment containing the cornea 2, iris 3, ciliary body 4 and lens 5; and the posterior segment containing the choroid 6, retina 7 and vitreous 8. The outer shell of the eye is comprised of four main layers, said layers from outside to inside are: the conjunctiva, the thin, loosely adhered outer cover of the eye; the sclera 9, the white collagenous tissue making up the major structural component of the eye; the choroid 6, the vascular layer of the eye; and the retina 7, the sensory layer of the eye. The two targets being assessed by the invention are the potential space between the sclera and the choroid, the suprachoroidal space 10, and the potential space between the retina and the choroid, the sub-retinal space 11.

Figure 2:
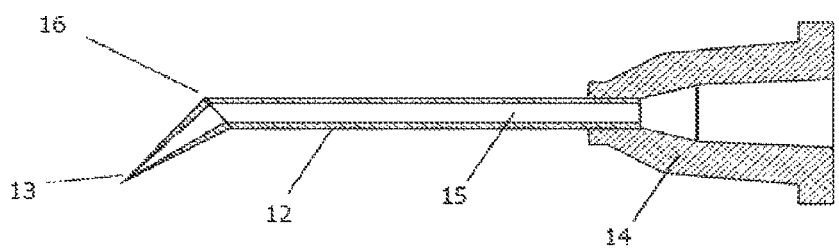
FIG. 2 is a schematic of a device according to one embodiment of the invention comprising an angled tip.

In one embodiment (FIG. 2), the device according to the invention comprises a main shaft 12 with a distal end and a proximal end in internal communication with each other, such as, through a lumen 15. The distal end may comprise a beveled, sharpened tip 13 configured to penetrate ocular tissues with a minimum amount of force to create a tract or passage in the sclera. Tip 13 may comprise a point, a single bevel or multiple bevel surfaces. Bevels (the angle swept by the surfaces with the pointed tip at the apex) in the range of 10°-30° are preferred. The proximal end may comprise attachment receiver 14 such as a female Luer connector to allow for attachment of a syringe or other delivery apparatus. The main shaft 12 may comprise a hollow tube with a lumen 15. The shaft may have an outer diameter in the range of 41 gauge (0.0028 inch, 0.071 mm) to 20 gauge (0.035 inch, 0.89 mm) and an inner lumen diameter in the range of 0.002 inch (0.05 mm) to 0.023 inch (0.58 mm). The tube may comprise a metal such as tungsten, Nitinol (nickel-titanium alloy) or stainless steel; or a polymer such as polyetheretherketone (PEEK), polycarbonate, nylon or other similar structural engineering polymer. In one embodiment, the shaft may incorporate an angle or bend 16 near the distal end. The angle or bend is used to direct the distal tip from an initial approach perpendicular to the surface which allows for ease of entry, to a path which enters the suprachoroidal space or sub-retinal space approximately tangential to the curve of the eye. The bend angles may be in the range of 10°-60°, and preferably in the range of 20°-40°.

Figure 3:
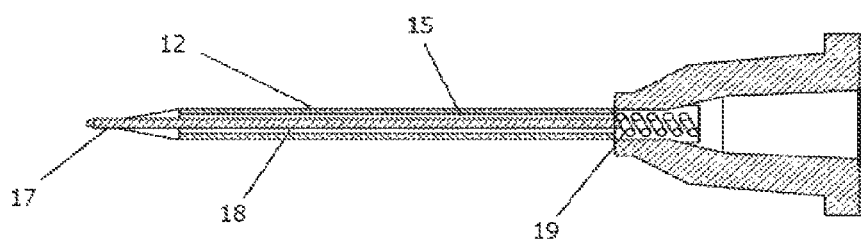
FIG. 3 is a schematic of a device according to one embodiment of the invention comprising a guard element disposed in the lumen of the main shaft.

In another embodiment (FIG. 3), the shaft 12 may incorporate a mechanical guard to displace the choroid or retina from the sharpened distal tip. The mechanical guard may comprise an element 18 slideably disposed within the lumen 15 or an element disposed outside the diameter of the shaft 12. In the first instance, the guard 18 may comprise a blunt tip, elongated member 17, slideably disposed within the lumen 15 of the main shaft, having the guard distal tip extending beyond the distal tip of the main shaft and connected to the body of the device by a compression spring 19. The guard member 17 is spring loaded in a manner such that when the blunt device tip encounters tissues with substantial mechanical resistance, such as the sclera, the guard member is compressed backwards into the lumen, exposing the sharpened tip of the device and allowing it to penetrate tissues. During advancement within the tissues with the sharpened tip, the spring provides a forward directed force to the guard. When the distal tip encounters an open space or tissues that may be displaced such as the choroid in the case of the suprachoroidal space or the retina in the case of the sub-retinal space, the guard member 17 again extends forward due to the reduced resistance against the tip, ahead of the sharpened tip of the device and thereby displacing the tissues away from the tip of the device. The tissue displacement spring rate for the guard is in the range of about 0.3 lb./in (0.05 N/mm) to 2.8 lb./in (0.50 N/mm) and preferably in the range of 4.6 lb./in (0.8 N/mm) to 1.4 lb./in (0.25 N/mm). The guard member may have a configuration to allow the flow of fluid through the lumen of the main shaft once the guard is deployed and the underlying tissue is displaced. Alternatively, the guard may be configured as part of a removable assembly such that once the sharpened tip is in the appropriate space, the guard assembly may be removed and a delivery device, such as a syringe may be attached to the proximal end to deliver a fluid, therapeutic agent or diagnostic substance.

Figure 4:
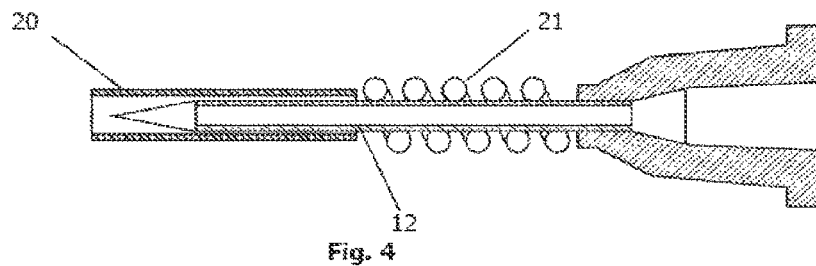
FIG. 4 is a schematic of a device according to one embodiment of the invention comprising a tubular guard element disposed about the outside of the main shaft.

Referring to FIG. 4, the mechanical guard may comprise a tube 20 slideably disposed on the outside of the main shaft 12, which is also connected to the main shaft by a compressive element 21 such as a metallic or plastic spring, a polymer with elastic properties or a compressible gas reservoir. The tube is sized and configured to enter the tract or passage in the sclera with the main shaft. The device is configured such that the compressive element 21 exerts a force on the mechanical guard to provide a forward directed force at the distal end. In a similar manner to the previous embodiment described in connection with FIG. 3, when the tubular guard encounters tissue with mechanical resistance greater than the choroid or retina (e.g. sclera) the tube is displaced backwards (in the proximal direction), exposing and allowing the sharpened tip to penetrate the tissues. When the guard enters the tissues and encounters an open space or soft tissue such as the choroid or retina, it slides forward due to the reduced resistance, effectively blocking the distal tip of the device from further penetration.

In another embodiment, the guard may comprise a flowable or fluidic guard, composed of either a fluid or gas, which is delivered through the distal end of the device to provide a forward directed force and displace the choroid as the device distal tip enters the suprachoroidal space or the displacement of the retina as the distal tip enters the sub-retinal space. The guard may comprise a fluid, such as sterile water, saline, balanced salt solution, silicone oil, surgical viscoelastic, polymer solution or an ophthalmically acceptable perfluorocarbon fluid such as perfluoro-n-octane. Alternately, the guard may comprise a gas, such as air, nitrogen ($N_2$), carbon dioxide ($CO_2$), or gases used in ophthalmology such as sulfur hexafluoride ($SF_6$) or octafluoropropane ($C_3F_8$). Additionally the guard may comprise the fluid or gas of a therapeutic or diagnostic formulation to be delivered. Fluid or gas volumes and pressures to sufficiently displace the tissues without overinflating the eye but allowing enough space to safely perform an injection are usefully in the range of about 10 microliters to 500 microliters volume and about 0.05 mm Hg to 52 mm Hg gauge pressures, and preferably in the range of 50 microliters to 250 microliters volume and 4 mm Hg to 30 mm Hg gauge pressure. Such a fluidic guard may be delivered through a syringe filled with the fluid or gas attached to the proximal connector.

Figure 5:
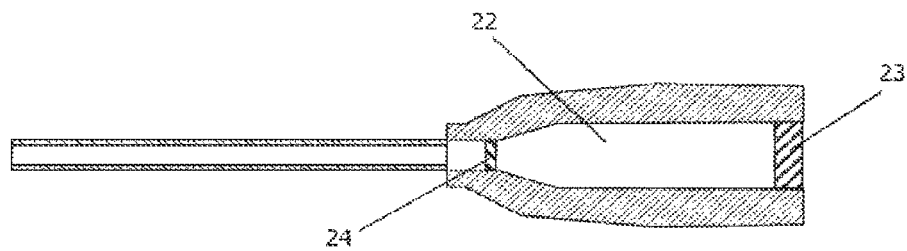
FIG. 5 is a schematic of a device according to one embodiment of the invention comprising a reservoir element.

In another embodiment (FIG. 5), the device comprises a pressurized reservoir 22 for the delivery of a precise amount of the fluidic guard. The reservoir may be configured to deliver the material at a precise pressure and flow rate to achieve displacement of the choroid or retina, while preventing over-inflation of the space. The reservoir may be adapted to be prefilled to a desired volume and pressure. This may be accomplished, for example, by incorporating entries 23 to fill the reservoir, such as injection ports, valves, heat sealable caps or similar entries to allow sterile transfer of materials to the reservoir, which may be accomplished during the manufacture of the device. The reservoir may further be adapted to allow controlled access to the main shaft lumen to allow for the injection of the contents of the reservoir to the target site. Access may be achieved by a septum 24, seal or plug at the distal end of the reservoir, configured to accommodate an activating mechanism of the device. In another embodiment, the reservoir may be configured to deliver a therapeutic or diagnostic substance with a flowable material to act as a fluidic guard.

Figure 6:
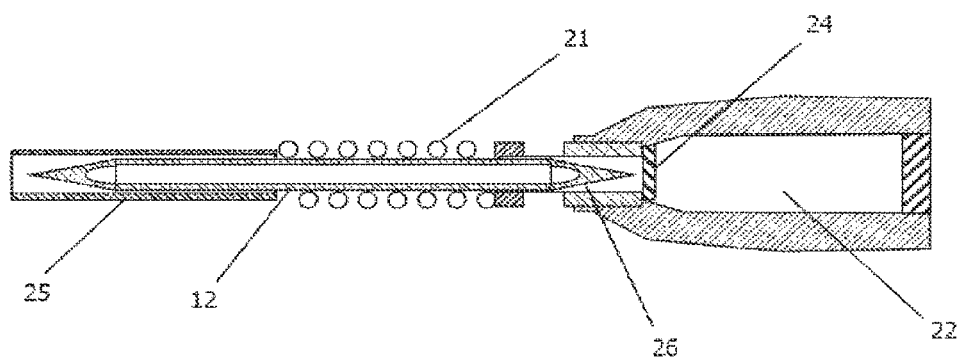
FIG. 6 is a schematic of a device according to one embodiment of the invention comprising a sealed reservoir activated by piercing said seal.

The device may be adapted to automatically activate the delivery of the fluid or gas, or the delivery may be activated and controlled by the user. Automatic delivery may be triggered by a plate or stop, which, when the stop comes in contact with the surface of the eye, triggers the delivery of the fluid or gas. In one embodiment (FIG. 6) the stop may comprise a tubular element 25 disposed about the outside of the main shaft 12. The element 25 may be attached to the main body by means of a compressive element 21 such as a metallic or plastic spring, a polymer with elastic properties, or a compressible gas reservoir. The main shaft may comprise the activating mechanism to release reservoir material. The mechanism may comprise a sharpened tip 26 at the proximal end of the main shaft configured to pierce a septum or seal 24 on the reservoir 22.

Figure 7:
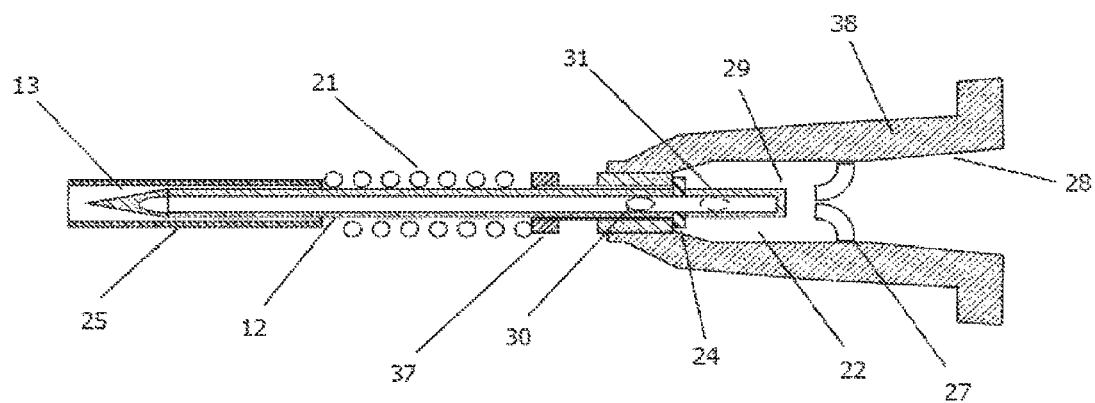
FIG. 7 is a schematic of a device according to one embodiment of the invention comprising a spring loaded distal element on a sliding shaft with a valve mechanism.

In another embodiment (FIG. 7), the device comprises a main shaft 12 with a distal, beveled tip 13 and a trigger stop 37 disposed about the shaft. The main shaft is disposed within a proximal hub 38 containing a reservoir 22. The reservoir comprises a check valve 27 and Luer connector 28 on the proximal end to receive attachments to fill the reservoir. The distal end of the reservoir contains a polymer septum 24. The proximal end 29 of the main shaft is sealed and disposed through the septum. The proximal end of the main shaft comprises a hole 30 or valve port on the side, the port being distally displaced from the septum when the device is not activated. The reservoir is prefilled with a guard fluid or gas, or a therapeutic agent by a syringe or gas line connection. A tubular element 25 is disposed about the outside of the main shaft distal portion, the element attached to the main shaft by a compression spring 21. The spring constant is in the range of 0.29 lb./in (0.05 N/mm) to 14.3 lb./in (2.5 N/mm) and preferably in the range of 0.97 lb./in (0.17 N/mm) to 3.37 lb./in (0.59 N/mm). The device is adapted such that upon contact with the surface of the eye, the distal tubular element 25 translates rearward (in the proximal direction) compressing the spring element against the trigger stop 37 until the force reaches a predetermined value set by the spring rate and the coefficient of friction of the septum against the main shaft. Upon reaching the appointed force value, continued advancing pressure on the device hub translates the main shaft rearwards, displacing the port 30 proximally to the reservoir side of the septum 31, releasing the contents of the reservoir to exit the distal tip. The trigger stop may also be configured to limit the rearward travel of the main shaft beyond the point where the reservoir contents are released. The force value combination of spring rates and septum friction coefficients may be selected to trigger at a specific penetration depth either when entering the suprachoroidal space or the subretinal space. The depth of penetration is in the range of about 0.02 inches (0.5 mm) to 0.157 inches (4 mm).

Figure 8:
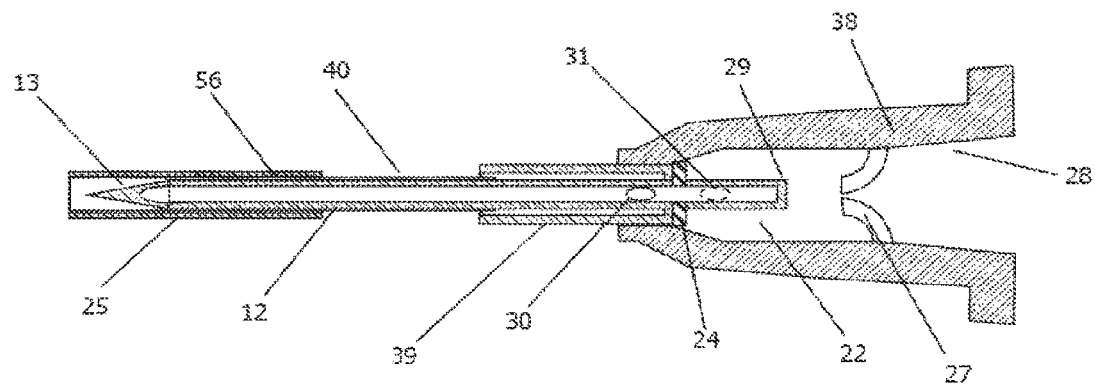
FIG. 8 is a schematic of a device according to one embodiment of the invention comprising a sliding distal element on a sliding shaft with a valve mechanism.

In another embodiment (FIG. 8), the device comprises a main shaft 12 with a distal, beveled tip 13 and a tubular trigger stop 39 disposed about the shaft. The trigger stop has an inner diameter larger than the outer diameter of the main shaft and is attached to the main shaft at the proximal end such that the gap between the trigger stop and the main shaft faces toward the distal end. The main shaft is disposed within a proximal hub 38 containing a reservoir 22. The reservoir comprises a check valve 27 and Luer connector 28 on the proximal end to receive attachments to fill the reservoir. The distal end of the reservoir contains a polymer septum 24. The proximal end 29 of the main shaft is sealed and disposed through the septum. The proximal end of the main shaft comprises a hole 30 or valve port on the side, the port being distally displaced from the septum when the device is not activated. The reservoir is prefilled with a guard fluid or gas, or a therapeutic agent by a syringe or gas line connection. A tubular element 25 is disposed about the outside of the main shaft distal portion, the element 25 comprising a thicker walled distal portion 56 and a thin walled proximal portion 40. The thin walled portion is sized to slide between the tubular trigger stop and the main shaft.

The device is adapted such that upon contact with the surface of the eye, the distal tubular element 25 translates rearward until the proximal end of the thick walled portion comes in contact with the trigger stop 39. Continued advancing pressure on the device hub translates the main shaft rearwards, displacing the port 30 proximally to the reservoir side of the septum 31, releasing the contents of the reservoir to the lumen of the main shaft. The trigger stop may be configured to limit rearward travel. The lengths of the device components and the gap between the distal tubular element 25 and the trigger stop 39 are adapted to provide a specific depth of penetration of the main shaft distal beveled tip 13.

The depth of penetration to enter the suprachoroidal or subretinal space is in the range of about 0.02 inches (0.5 mm) to 0.157 inches (4 mm).

Figure 9:
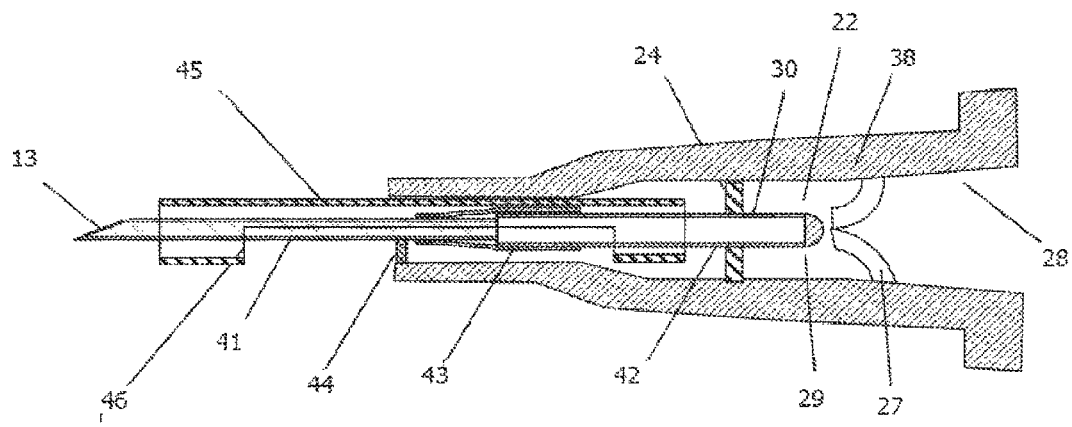
FIG. 9 is a schematic of a device according to one embodiment of the invention comprising a fixed shaft and a sliding outer element connected to a valve mechanism.

In another embodiment (FIG. 9), the device according to the invention comprises a tubular distal shaft 41 with a distal beveled tip 13 and tubular proximal shaft 42. The shafts 41, 42 are slideably disposed with each other and one shaft may be sized so as to slide inside or outside the other shaft. Proximal shaft 42 incorporates a sealed proximal end 29 and a hole or port 30 on the side. An elastomer seal 43 is disposed about the outside of the distal shaft 41 and proximal shaft 42, across the junction between the two and provides a seal to prevent fluid or gas escape while allowing linear motion between the shafts. The distal shaft is fixed in place to a proximal hub 38, by way of a cross-bar 44. An outer housing 45 is slideably disposed about the distal shaft and is attached to the proximal shaft. The outer housing comprises a slot or cut-out 46 to accommodate the cross-bar 44, allowing the outer housing and proximal shaft to slide independently of the fixed distal shaft 41. The proximal hub comprises a reservoir 22 with a polymer septum 24, a check valve 27 to allow pressurization of the reservoir and Luer connector 28 at the proximal end to receive attachments to fill the reservoir. The sealed proximal end 29 of the proximal shaft is disposed through the septum, such that during filling of the reservoir, the port 30 is distally displaced from the septum 24 thereby sealing the reservoir. The reservoir is prefilled with a guard fluid or gas, or a therapeutic substance by a syringe or gas line connection. The device is adapted such that upon contact with a tissue surface of the distal tip of the outer housing, the outer housing 45 and the proximal shaft 42 are translated rearward (in the proximal direction) displacing the port 30 proximally to the reservoir side of the septum 24, releasing the contents into the main shaft lumen.

Figure 10:
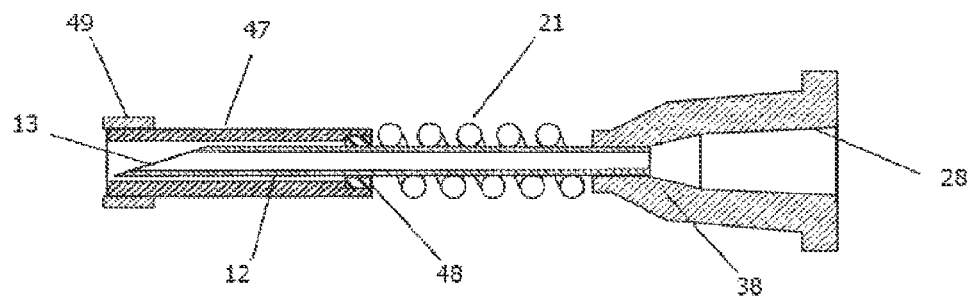
FIG. 10 is a schematic of a device according to one embodiment of the invention comprising a sealing element spring loaded about a main shaft.

In another embodiment (FIG. 10), in conjunction with a fluidic guard, the device may also comprise a sealing element directed at the site of conjunctiva and sclera penetration. The seal is designed to prevent leakage of the fluid or gas through the tissue tract created by the device which would reduce the amount of fluid or gas directed at the underlying choroid or retina to displace the underlying tissue to prevent penetration by the pointed or beveled tip of the main shaft. The seal may be incorporated on the device, for example as an outer tubular sleeve 47 slideably disposed over the main shaft 12 which incorporates a beveled tip 13. The tubular sleeve incorporates an internal seal 48 to seal the sleeve against the main shaft to prevent fluid or gas reflux between the sleeve and shaft. The proximal end of the main shaft is disposed in a hub 38 comprising a Luer connector 28 for attachment of a fluid or gas delivery mechanism such as a syringe. The distal end of the sleeve acts to seal against the conjunctiva at the surface of the eye or the scleral surface after minor dissection. The tubular sleeve is preferred to have a diameter at the tissue surface to provide sufficient area surrounding the site of tissue penetration to provide an effective seal against the pressure of the fluidic guard. The outer diameter of the tubular sleeve may range from 0.04 inch (1.0 mm) to 0.12 inch (3.0 mm) to provide adequate sealing area on the surface of the eye without unduly obscuring the visualization of the site. The tubular sleeve may be aided by a spring mechanism 21 to provide a sealing force against the eye surface as the inner main shaft penetrates the outer tissues of the eye. The spring constant is the range of 0.29 lb./in (0.05 N/mm) to 14.3 lb./in (2.5 N/mm) and preferably in the range of 0.97 lb./in (0.17 N/mm) to 2.0 lb./in (0.35 N/mm). The spring mechanism may be a mechanical spring or alternatively a gas reservoir or elastomeric component to provide spring-like function. The distal end of the tubular sleeve 47 may incorporate rubber, elastomeric or deformable materials 49 to conform to the tissue surface and aid the sealing effect and reduce the required sealing area.

Figure 11:
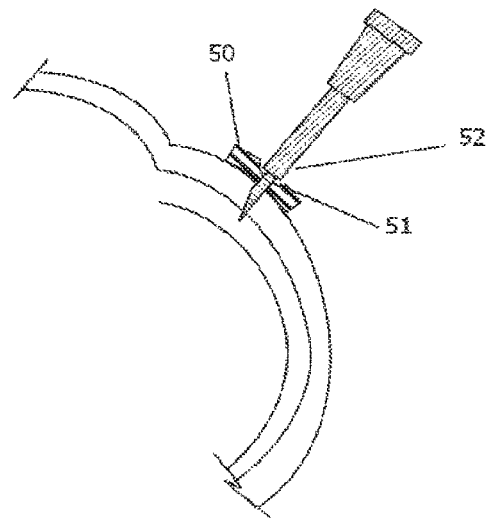
FIG. 11 is a schematic of a device according to one embodiment of the invention comprising a separate sealing mechanism disposed upon the surface of the tissues and an injecting element inserted therethrough.

Alternatively, (FIG. 11) the sealing element may be a separate component 50 that is placed on the eye and the device used to penetrate the seal and underlying conjunctiva and sclera. The separate component may be a soft polymer, rubber or elastomer of a thickness to provide the appropriate main shaft length through the conjunctiva and sclera to reach the target suprachoroidal or sub-retinal space. The separate component may have a target region 51 of decreased thickness sized to fit the outer dimensions of the device when the device is placed on the component to aid location and stabilization of the device when placing the device on the eye, penetrating the seal, and penetrating the overlying conjunctiva and sclera. The separate component may also be of the appropriate thickness to trigger release of the guard fluid or gas once the distal lumen of the main shaft has entered the seal. Mechanical features of the separate component such as a flange, sleeve or rod extending toward the device as it is placed may trigger release of the guard fluid or gas. The device may incorporate a stop 52, sized to fit within the target region 51 of the sealing element which controls the depth of entry of the distal tip of the device.

The device may also comprise indicators to show when the guard has been deployed to protect the underlying choroid and retina, and that a pathway to the suprachoroidal space or sub-retinal space has been established. An indicator may comprise a depth indicator of the mechanical guard or a volume or flow indicator of the reservoir. An indicator may also be coupled to a sensor to initiate a visual or audible signal to the user to limit penetration with the device and indicate that the eye is ready for injection of materials to the suprachoroidal or sub-retinal space.

Figure 12:
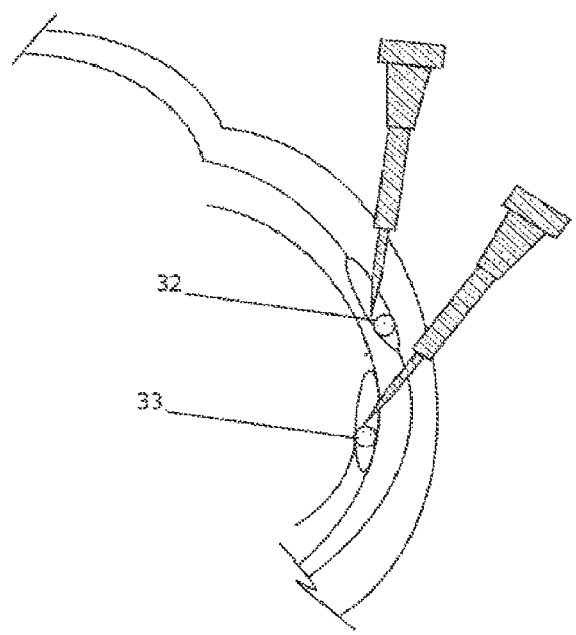
FIG. 12 is a schematic depiction of a device performing injections into the suprachoroidal and subretinal spaces.

Referring to FIG. 12 the materials for injection into the suprachoroidal space 32 or sub-retinal space 33 may comprise an implant, a drug solution, drug suspension, or drug containing material such as a gel or solid implant, gene therapy agents, stem cells or cell therapy agents. In addition, the device may comprise apparatus to extend a flexible tubular element within the suprachoroidal space or sub-retinal space after deployment of the guard, toward the posterior end of the eye to extend the distal lumen and administer materials to a location closer to the posterior region of the eye. The flexible tubular element is preferred to have a rounded atraumatic distal end to minimize trauma to the choroid or retina.

Figure 13:
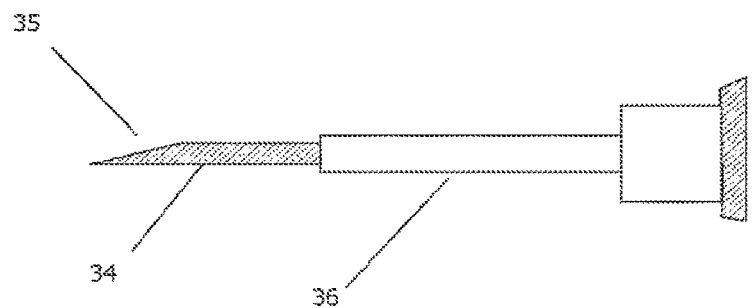
FIG. 13 is a schematic of a device according to one embodiment of the invention comprising an access port on a trocar.
Figure 14:
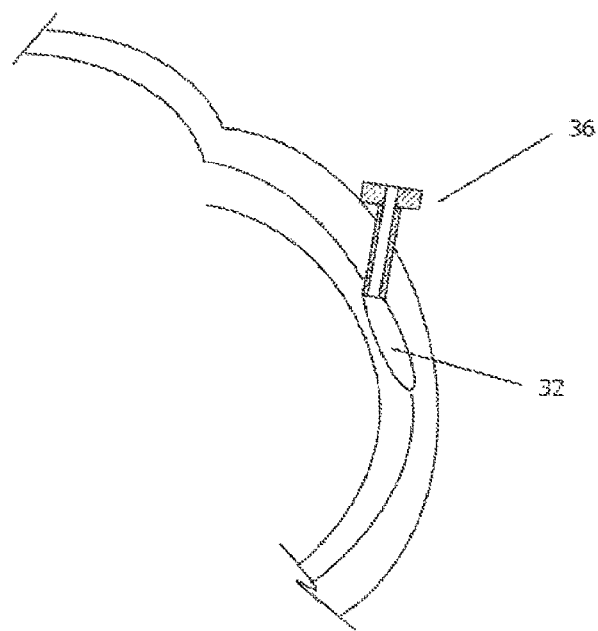
FIG. 14 is a schematic depiction of an access port placed in suprachoroidal space with a device.

In another embodiment (FIG. 13), the device may comprise a distal end and a proximal end in communication with each other as previously described in conjunction with an outer sleeve that is implanted into the sclera. The body of the device may be in the form of a solid member or hollow tubular member 34 with a sharp tip 35. The device may incorporate a mechanical or fluidic guard as previously described to displace the choroid for access to the suprachoroidal space or to displace the retina for access to the subretinal space. The device further comprises a thin walled sleeve 36 slideably disposed about the outer diameter of the body of the device. The sleeve is advanced into the tissues as the device is placed. The sleeve 36 remains behind when the device is removed from the eye. As shown in FIG. 14, sleeve 36 functions as an access port or introducer, in communication from the outside of the eye to the suprachoroidal space 32 or sub-retinal space, for the introduction of other devices such as needles, cannulae or catheters into the space during surgery. The sleeve is typically sized at about 0.0045 inch (0.11 mm) to 0.0355 inch (0.90 mm) outer diameter with a wall thickness in the range of about 0.0005 inch (0.12 mm) to 0.002 inch (0.5 mm) and a length in the range of about 0.60 inch (1.5 mm) to 0.195 inch (5 mm). The sleeve may also have an enlarged diameter or flange at the proximal end to secure the proximal end at the surface of the eye. The sleeve may comprise metals such as nitinol, stainless steel, tungsten or polymers such as polyimide, nylon, polyamide, PEEK, or polycarbonate.

The device may further comprise a feature to limit the depth of penetration of the distal tip. This feature may comprise a mechanical stop or flange disposed about the outer diameter of the device body which limits travel by the stop encountering the surface of the eye. The stop may be in the form of a flat surface which may be disposed perpendicularly to the body of the device or may be disposed at an angle to the body such that the angle approximates the angle of the surface of the globe in relation to the angle of entry by the device itself. The stop configurations may be incorporated into the mechanism used to guard the device, such as the outer tubular member previously described. The stop may be adjustable to allow the user to tailor the use of the device to different tissue thicknesses, for example in different regions of the eye.

Figure 15:
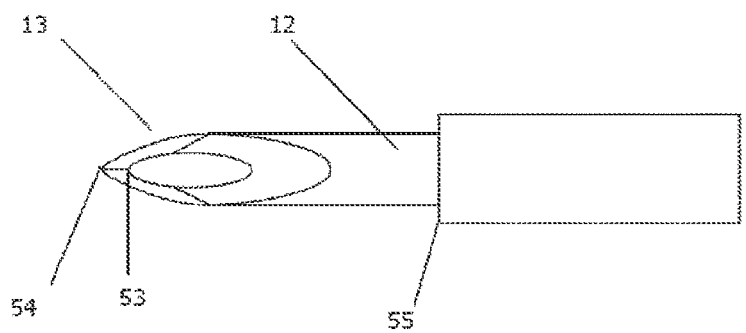
FIG. 15 is a schematic depiction of a main shaft of a device according to the invention with a beveled tip and the tissue contacting surface of the device.

In many embodiments, as shown in the top view, FIG. 15, the main shaft 12 with a pointed or beveled distal end 13 will have the appropriate exposed length to access the target site. In the case of access to suprachoroidal space, the length is preferred to be sufficient to expose at least the most distal portion of the lumen to the suprachoroidal space when the device is placed through the conjunctiva and sclera to allow the guard to enter the space and displace the underlying choroid. From anatomic considerations based upon minimum combined tissue thickness of the conjunctiva and sclera of 0.015 inch (0.38 mm), this length to the distal end of the lumen is at minimum 0.025 inch (0.65 mm). In the case of access to the sub-retinal space, the main shaft length is preferred to have a length to expose the most distal portion of the lumen to the sub-retinal space when the device is placed through the conjunctiva, sclera and choroid. From anatomic considerations based upon the average combined tissue thickness of conjunctiva, sclera and choroid of 0.023 inch (0.58 mm), this length to the distal end of the lumen is at minimum 0.023 inch (0.58 mm). To minimize damage to the underlying tissue distal to the desired target space, the main shaft length is preferred to be no more than the thickness of the proximal tissue overlying the target space plus the amount of tissue displacement of the underlying tissue due to the guarding element. For access to the suprachoroidal space, this maximum length is approximately 0.108 inch (2.75 mm). For access to the sub-retinal space, this maximum length is approximately 0.118 inch (3.00 mm). When the device is used in conjunction with a sealing element, the preferred lengths are the effective lengths of the main shaft with respect to the distal edge 53 of the lumen and distal, beveled tip 54 to the distal, tissue contacting surface of the seal 55. In addition to the anatomical dimensions, the preferred functional lengths of the main shaft should also account for the mechanical characteristics of the tissues to be penetrated to account for tissue deformation during use of the device.

The following Examples are provided for the purpose of illustrating particular devices and methods according to the invention. These Examples are not intended to limit the scope of the invention in any manner.

EXAMPLES

Example 1

A device according to one embodiment of the invention was fabricated and tested for its ability to successfully penetrate the sclera and displace the choroid for access to the suprachoroidal space. The device was comprised of a needle as the main shaft and a spring loaded guard element. The needle element was comprised of a 27 gauge (0.4 mm)×0.5 inch (12.7 mm) short bevel hypodermic needle (Monoject, Covidien Inc) as the main shaft. The needle tip bevel angle was 18°, and the proximal end was a standard Luer lock connector. The spring loaded guard element was comprised of a stainless steel wire 0.007 inch (0.18 mm) diameter sized to fit slideably within the lumen of the needle element main shaft and of a length so that the distal tip of the wire extended beyond the distal needle tip by 0.004 inch (0.1 mm). The tip of the wire was rounded so as not to have any sharp edges. The wire was welded into a larger stainless steel tube, sized to slideably fit inside a compression spring. A spring perch was welded to the distal end of said tube. A spring with an inner diameter of 0.049 inch (1.25 mm) and a spring rate of 0.7 lb./in (0.12 N/mm) was placed over said tube. A second outer tube, sized to fit slideably about the spring tube and with an outer diameter larger than the spring outer diameter was placed about the spring tube, to act as a proximal stop for the spring. The wire was inserted into the lumen of the needle element. A Touhy-Borst Luer connector was attached to the needle Luer connector, and then tightened about the outer tube to hold it in place. This spring assembly allowed the wire to move rearward inside the needle.

A human cadaver eye was used for the experiment. The guard wire tip was placed against the tissue surface and the device advanced slowly into the tissues. The guard tip was seen to retract against the spring pressure, allowing the needle tip to enter the tissues. When the needle had been inserted approximately 0.6 inch (1.5 mm) the advancement was stopped. Using a high resolution optical coherence tomography (OCT) imaging system, the device placement was imaged. The needle tip could be clearly seen in the suprachoroidal space with the guard tip extending beyond the needle tip and displacing the choroid

Example 2

A device according to one embodiment of the invention was fabricated and tested for its ability to successfully penetrate the sclera and displace the choroid for access to the suprachoroidal space. The device was comprised of a stainless steel tubular main shaft, 0.79 inches (20 mm) long and 0.016 inches (0.4 mm) outer diameter and 0.008 inches (0.2 mm) inner diameter with a sharp 12° beveled tip. The main shaft was bonded proximally into a plastic female Luer connector. A mechanical guard element comprised of a distal thin walled polyimide tube with an inner diameter 0.0165 inches (0.42 mm) and outer diameter of 0.0175 inches (0.45 mm) was bonded to a proximal stop 0.04 inches (1.0 mm) in diameter. The distal end of the polyimide tubing was beveled to allow for entry into the tissues. The guard member was loaded onto the main shaft with a stainless steel spring of 0.017 inches (0.43 mm) inner diameter with the spring wire diameter of 0.005 inches (0.13 mm) between the guard and the plastic hub, disposed about the main shaft. The device was tested using a human cadaver eye. The tip of the device was inserted into the sclera and advanced forward. The mechanical guard was pushed rearward, allowing the sharp main shaft tip to enter the scleral tissues. With continued advancement, the guard element was also advanced into the sclera. When the distal tip of the main shaft entered the suprachoroidal space, the spring force advanced the guard element ahead of the main shaft tip, displacing the choroid. Optical Coherence Tomography (OCT) imaging confirmed the guard element tip location within the suprachoroidal space.

Example 3

A device according to one embodiment of the invention was fabricated and tested for its ability to successfully penetrate the sclera and displace the choroid for access to the suprachoroidal space. The device was comprised of a metal main shaft 0.79 inches (20 mm) long and 0.016 inches (0.41 mm) outer diameter and 0.008 inches (0.2 mm) inner diameter with a sharp beveled tip. The main shaft was sealed at the proximal end and a side hole was made approximately 0.197 inches (5 mm) from the end. The device distal tip was angled to 30° and 0.059 inches (1.5 mm) length. The device featured a spring retractable metal sleeve disposed about the main shaft distal tip and that acted as a mechanism to trigger the infusion of gas into the suprachoroidal space when it retracted. The spring proximal end was attached to a metal sleeve that added structural support of the main shaft and Luer attachment. A Luer connector with a polymer septum was secured to the proximal end of the main shaft such that the main shaft penetrated the septum with the side hole distal to the septum. A check valve assembly was attached to the Luer connector to serve as a gas filled reservoir providing a means of infusing gas into suprachoroidal space to displace the choroid. The device was tested using a human cadaver eye. The device angled tip was inserted into the sclera near the pars plana and advanced until the angled tip was positioned in the suprachoroidal space. Upon contact with the scleral surface, the distal metal sleeve was pushed rearward until the spring force overcame the frictional force of the main shaft in the septum, which drove the proximal end of the main shaft through the septum positioning the side hole above the septum. Gas within the chamber was released through the main shaft, out the tip, and into the suprachoroidal space. Optical Coherence Tomography (OCT) imaging confirmed the tip location within the suprachoroidal space and release of the fluidic air guard, displacing the choroid to prevent contact of the choroid with the tip.

Example 4

A device according to one embodiment of the invention was fabricated and tested for its ability to successfully penetrate the sclera and displace the choroid for access to the suprachoroidal space. The device main shaft was comprised of a 0.016 inches (0.41 mm) outer diameter and 0.008 inches (0.2 mm) inner diameter and 0.984 inches (25 mm) long injection needle with sharp bevel straight tip and proximal Luer connector. Additional design features included a metal proximal and distal outer housing assembly, 0.028 inch (0.7 mm) diameter by 0.472 inches (12 mm) long segments connected by a 0.197 inches (5 mm) long coil spring. The distal outer housing segment provided a spring retractable protective sleeve and insertion depth stop at the main shaft distal tip. The proximal outer housing segment was attached to the main shaft for improved device rigidity. The proximal main shaft open end was inserted into a polymer septum of a pressurized fluid filled reservoir. The device was tested using a human cadaver eye. Upon inserting the device distal tip through the sclera and into the suprachoroidal space, the proximal main shaft moved backward axially, pierced through the septum and into the fluid reservoir. The reservoir content was then released into the open end of the proximal main shaft and discharged out the distal tip and into the suprachoroidal space. The resulting choroid displacement to prevent contact of the distal tip with the choroid was monitored and confirmed in real time with ultrasound imaging.

Example 5

A device according to one embodiment of the invention was fabricated and tested for its ability to successfully penetrate the sclera and displace the choroid for access to the suprachoroidal space. The device was comprised of a metal main shaft 0.79 inches (20 mm) long and 0.016 inches (0.41 mm) outer diameter and 0.008 inches (0.2 mm) inner diameter with a sharp beveled tip. The main shaft was sealed at the proximal end and a side hole was made approximately 0.197 inches (5 mm) from the end. A Luer connector with a polymer septum was secured to the proximal end of the main shaft such that the main shaft penetrated through, with the side hole distal to the septum. A check valve assembly was attached to the Luer connector providing for a Tillable gas reservoir of approximately 100 microliters volume. A metal sleeve with an inner diameter of 0.020 inches (0.51 mm) and an outer diameter of 0.028 inch (0.71 mm) was disposed about the main shaft and attached to it near the proximal end. The sleeve acted as a mechanism to trigger the release of the gas filled reservoir into the suprachoroidal space when forced rearward, translating the side port to the reservoir side of the septum. An access port element 0.0065 inch (0.17 mm) inner diameter and 0.0005 inch (0.012 mm) wall thickness comprised of polyimide was disposed about the outside of the main shaft and inserted under the metal sleeve. The device was tested using a human cadaver eye. The device tip was inserted into the sclera near the pars plana and advanced until the tip entered the suprachoroidal space and the sleeve triggered the release of the reservoir, injecting gas to displace the choroid. The port element was then advanced forward into the suprachoroidal space. Optical Coherence Tomography (OCT) imaging confirmed the distal end of the port location within the suprachoroidal space and a fluid injection was made through the port, while confirming inflation of the suprachoroidal space on imaging.

Example 6

Devices fabricated according to Example 5 were tested to determine the delivered pressure of a gaseous fluidic guard based upon the amount of gas charged into the reservoir and to determine the amount of choroidal displacement achieved due to the gas charge in the reservoir. A diaphragm pressure transducer (PX26-100GV, Omega Engineering) was modified to place a Luer injection port into the transducer port, minimizing the dead volume of the transducer. The transducer was connected to a digital readout (DP-41S, Omega Engineering) and then calibrated to read out in mm Hg. The main shaft needle tip of a device under test was inserted into the injection port of the pressure transducer. The check valve was removed and the Luer connector advanced to open the internal valve mechanism and equalize the system pressure. The Luer connector was then pulled back, closing the internal valve and the check valve was re-installed. A 1 cc syringe was filled with a volume of air, attached to the check valve Luer connector of the device and then expelled to charge the reservoir. The device was advanced to open the internal valve and the gauge pressure of the delivered gas was read from the digital readout. Syringe volumes of 0.1 cc to 0.7 cc were tested. However the actual fill volume of the reservoir was less than the syringe volume. Due to the fixed volume of the reservoir and the limited ability of a manual syringe to compress the gas, a small amount of gas refluxed into the syringe as evidenced by the rebound of the syringe plunger after full depression of the plunger.

Additional devices were tested in-vitro using both human and porcine cadaver eyes, and in-vitro using a live porcine animal model. A 1 cc syringe was used to load the device reservoirs with 0.2, 0.4 or 0.6 cc of air. The devices were advanced into the eyes, activating the internal valve and releasing the reservoir contents, and the resultant choroidal displacement was measured using high frequency ultrasound imaging. The table below shows the experimental results.

TABLE 1

| Syringe Charge Volume (cc) | Average Gauge Pressure (mm Hg) Delivered | Average Choroid Displacement (mm) - Human Cadaver Eyes | Average Choroid Displacement (mm) - Porcine Cadaver Eyes | Average Choroid Displacement (mm) - Live Porcine Eyes |
|---|---|---|---|---|
| 0.1 | 4.7 | — | — | — |
| 0.2 | 8.3 | 0.63 | 0.75 | 0.34 |
| 0.3 | 11.6 | — | — | — |
| 0.4 | 14.8 | 1.01 | 0.86 | 0.61 |
| 0.5 | 18.1 | — | — | — |
| 0.6 | 21.3 | 1.10 | 1.00 | 0.76 |
| 0.7 | 24.4 | — | — | — |

Example 7

A device fabricated according to Example 5 was tested for its ability to deliver a therapeutic agent to the suprachoroidal space. Porcine cadaver eyes were used in the experiment. The device reservoir was charged with 0.5 cc of air as the fluidic guard material. A syringe containing 0.25 cc of triamcinolone acetonide (TA), a corticosteroid particulate suspension (Kenalog 40, Bristol Meyers Squib), was attached to the proximal Luer connector of the device. The device was placed against the sclera of the cadaver eye and advanced until the distal tip entered the suprachoroidal space and discharged the reservoir gas, displacing the choroid away from the tip. After entering the space, the syringe plunger was depressed, injecting the TA suspension. High frequency ultrasound imaging confirmed that the suprachoroidal space had been opened and that TA particles were visible in the space. A perfusion system was set-up consisting of a reservoir of phosphate buffered saline (PBS) on a variable height platform. Tubing was attached to a port at the bottom edge of the reservoir, leading to a shut-off valve and a small tube with a Luer connector at the end. A 30 gauge (0.3 mm) hypodermic needle was attached to the reservoir Luer connector. The reservoir was elevated to provide 0.29 PSI (15 mm Hg) pressure. The 30 gauge needle was inserted through the cornea and into the anterior chamber to provide perfusion to the cadaver eye. The eye was allowed to perfuse for 6 hours at constant pressure. After the perfusion, the sclera of the eye over the injection site was dissected and removed. Examination under a light microscope showed the depot location of the TA particles on the choroid surface around the injection site. Also noted was a stream of particles extending approximately 0.55 inches (14 mm) posterior from the injection site, indicating a flow directed movement of the injectate towards the posterior pole of the eye.

Example 8

In another test, a device fabricated according to Example 5 was tested in the manner of Example 5, however the device reservoir was charged with the suspension steroid instead of air. A syringe with additional injectate was attached to the device. The device was advanced into the tissues and the reservoir fluid contents were discharged when the suprachoroidal space was reached, displacing the choroid and allowing for injection of the remaining fluid in the syringe into the suprachoroidal space. The injection location and tissue displacement was confirmed by ultrasound imaging.

Example 9

A device according to one embodiment of the invention was fabricated and tested for its ability to successfully penetrate the sclera and displace the choroid for access to the suprachoroidal space. The shafts and housings of the device were fabricated from 304 stainless steel hypodermic tubing. The device was comprised of a distal shaft of 0.016 inches (0.4 mm) outer diameter and 0.008 inches (0.2 mm) inner diameter by 0.75 inches (19 mm) long. The distal shaft had a standard hypodermic beveled tip with a main bevel angle of 12°. A shaft extension of 0.017 inches (0.43 mm) inner diameter and 0.025 inches (0.64 mm) outer diameter and 0.24 inches (6 mm) long was welded to the back of the distal shaft. A proximal shaft, the same diameter as the distal shaft and 0.42 inches (10.8 mm) long was cut and one end was welded shut. A side hole was ground through the wall 0.005 inches (0.13 mm) from the welded end. The distal end of the proximal shaft was slid inside the shaft extension on the distal shaft. A piece of 50 durometer silicone tubing 0.015 inches (0.38 mm) inner diameter by 0.027 inches (0.69 mm) by 0.2 inches (5 mm) long was placed over the junction between the proximal and distal shafts to seal the gap. An outer housing of 0.033 inches (0.84 mm) inner diameter by 0.046 inches (1.17 mm) outer diameter by 0.71 inches (18 mm) long was cut. Starting at 0.16 inches (4 mm) from the distal end of the outer housing and extending 0.5 inches (13 mm) long, one half of the outer housing was ground off leaving a half circle of tubing. An extension tube of 0.02 inches (0.51 mm) inner diameter by 0.032 inches (0.81 mm) outer diameter by 0.55 inches (14 mm) long was welded into the distal end of the outer housing, so as to act as the tissue contact portion of the moving assembly. The distal/proximal shaft assembly was placed inside the outer housing and a cross beam was welded to the distal shaft. The cross beam was adhesively bonded to a polycarbonate Luer connector. Inside the proximal end of the Luer connector, a solid disk of 50 durometer silicone rubber was inserted as a septum, with the tip of the proximal shaft just penetrating the septum so that the side hole was below the septum. A Luer check valve was attached to the Luer connector creating a sealed reservoir that could be filled from the Luer connector on the check valve.

The device was tested using a human cadaver eye. The reservoir was filled with air from a syringe. The device was placed against the tissue surface and advanced. As the outer housing assembly translated rearward, the side hole in the proximal shaft was translated to the reservoir side of the septum. The gas was released to displace the choroid and an injection of a suspension steroid (Kenalog 40, Bristol Meyers Squib) was made into the suprachoroidal space. The injection location was confirmed with ultrasound imaging.

Example 10

A device according to one embodiment of the invention was fabricated and tested for its ability to successfully penetrate the sclera and displace the choroid for access to the suprachoroidal space. The device was comprised of a commercial 27 ga (0.4 mm) by 0.5 inch (12.7 mm) short bevel hypodermic needle (Monoject 27 g×½ needle, Covidien Inc.) with a bevel main angle of 18° as the main shaft. A sliding seal assembly was fabricated as follows. Two pieces of polycarbonate tubing of 0.018 inches (0.46 mm) inner diameter by 0.060 inches (1.52 mm) outer diameter were cut, a long piece at 0.37 inches (9.4 mm) and a short piece at 0.08 inches (2.0 mm) long. The proximal end of the longer piece was counter-bored at 0.028 inches (0.71 mm) diameter by 0.05 inches (1.3 mm) deep. A piece of 50 durometer silicone tubing 0.015 inches (0.38 mm) inner diameter by 0.027 inches (0.69 mm) outer diameter by 0.04 inches (1.0 mm) long was cut and inserted into the counter-bore in the long tube as an inner seal. The short piece of polycarbonate tubing was then adhesively bonded to the long tube over the counter-bore to cap the inner seal in place. A piece of 50 durometer silicone tubing of 0.025 inches (0.64 mm) inner diameter by 0.047 inches (1.2 mm) outer diameter was placed over the distal end of the polycarbonate assembly to form an outer seal. The silicone tubing was placed such that the distal edge extended beyond the end of the polycarbonate tubing to serve as a seal against the tissue surface. A spring with a spring constant of 0.97 lb./in (0.17 N/mm) was placed over the hypodermic needle and the sealing assembly was slid over the needle.

The device was tested using human cadaver eyes. 1 cc syringe was filled with 0.1 cc of a suspension steroid (Kenalog 40, Bristol Meyers Squib) and the syringe attached to the device. The tip of the device was placed in contact with the tissues and light pressure was placed on the syringe plunger, effectively pressurizing the fluid pathway. The device was advanced into the tissues, keeping the sealing assembly in contact with the surface and maintaining pressure on the syringe plunger. When the needle tip advanced through the sclera a sufficient distance, the fluid was able to be injected, displacing the choroid and injecting the fluid into the suprachoroidal space. The injection location was confirmed with ultrasound imaging.

Example 11

A device according to one embodiment of the invention was fabricated and tested for its ability to successfully penetrate the sclera and displace the choroid for access to the suprachoroidal space. The device was comprised of an elastomeric tissue surface seal and a needle assembly as the main shaft with an integral depth stop. Two different models of the tissue surface seal were fabricated. The surface seal was comprised of 50 A durometer silicone rubber. Disc shaped base elements, 0.06 inch (1.6 mm) in thickness were fabricated, either 0.17 inch (4.4 mm) or 0.26 inch (6.6 mm) in diameter. Annular shaped seal elements of the same thickness were fabricated with an outer diameter of 0.17 inch (4.4 mm) and an inner diameter of 0.06 inch (1.52 mm). An annular element was adhesively bonded centrally to a base element, using room-temperature vulcanization (RTV) silicone adhesive. A main shaft needle assembly was fabricated comprising a 27 ga (0.4 mm)×0.5 inch (12.7 mm) short bevel hypodermic needle (Monoject, Covidien Inc.). A short length of polycarbonate tubing 0.018 inches (0.46 mm) inner diameter by 0.06 inches (1.52 mm) outer diameter was placed over the needle shaft as a depth stop. The tubing was cut to a length so that the exposed needle length was 0.13 inch (3.35 mm). In combination with the thickness of the tissue seal base, this length would provide for a needle length extending beyond the base element, to enter the tissues, of 0.07 inch (1.75 mm). The outer diameter of depth stop was sized to fit snugly and seal within the inner diameter of the annular seal element.

A human cadaver eye was prepared. The tissue surface at the pars plana was carefully dried and a tissue seal assembly was placed in contact with the surface and pressed down to effect a seal. A 1 cc syringe was filled with 0.1 cc of triamcinolone acetonide steroid suspension (Kenalog 40, Bristol Meyers Squib) and attached to the needle assembly. The needle tip was inserted into the center of the base element and advanced so that the depth stop entered the inner diameter of the annular element, scaling the fluid pathway. The needle advance was continued along with light pressure on the syringe plunger. When the depth stop reached the based element, and with the needle inserted to full depth, the injection was made. Ultrasound imaging confirmed the injectate in the suprachoroidal space. Both tissue seal devices, having different base element diameters, were successful.

Example 12

An experiment was performed to determine the range of lengths of the main shaft which would allow for injection into the suprachoroidal space in an eye. An adjustable stop was fabricated, sized to go over a 27 gauge (0.4 mm) hypodermic needle used as the main shaft. The distal end of the stop was 1.5 mm (0.06 inch) in diameter and the stop could be fixed in place so as to be able to have a set amount of needle tip extending beyond it. Two different needle bevels were tested. A standard hypodermic needle, with a nominal main bevel angle of 12 degrees (Precision Glide— 27 ga×½ inch, Becton-Dickenson) and a short bevel needle, with a nominal main bevel angle of 18 degrees (Monoject 250-27 ga×½ inch, Covidien) were used in the tests.

Human cadaver eyes were procured and ultrasound imaging was used to determine the average tissue thickness. The average surface tissue (scleral) thickness was 0.028 inch (0.70 mm) and the average full tissue thickness (sclera and choroid) was 0.045 inch (0.1.15 mm). Triamcinolone acetonide (Kenelog-40, Bristol Meyers Squib), a suspension steroid, was used as the injectate as the injected particles are clearly visible using ultrasound imaging. A 1 cc syringe was filled with 0.1 cc of triamcinolone for each test and attached to the test needle.

For each test, the adjustable stop was set to a preset needle length, as measured with a digital caliper. The needle tip was inserted into the tissue at the pars plana and with the adjustable stop fully pressed against the tissue surface and an injection of the triamcinolone was attempted. The injection was then evaluated using the ultrasound system to determine whether the injection was A) unsuccessful, i.e. no injection, too shallow, B) successful in injecting into the suprachoroidal space, or C) injected into the vitreous cavity, i.e. too deep. The following table presents the test results along with the distance between the distal end of the adjustable stop and the distal edge of the needle tip lumen. The results indicate a main shaft or needle length greater than 0.05 inch (1.25 mm) and less than 0.12 inch (3.00 mm) provide the best results for injection into the suprachoroidal space.

TABLE 2

| Needle Length (mm) | Standard Bevel Needle, Distal Stop to Distal Edge of Lumen (in/mm) | Standard Bevel Needle Result (A, B, C) | Short Bevel Needle, Distal Stop to Distal Edge of Lumen (in/mm) | Short Bevel Needle Result (A, B, C) |
|---|---|---|---|---|
| 0.25 | 0.002/0.06 | A | 0.003/0.08 | A |
| 0.50 | 0.012/0.31 | A | 0.013/0.33 | A |
| 0.75 | 0.022/0.56 | A | 0.023/0.58 | A |
| 1.00 | 0.032/0.81 | A | 0.033/0.83 | A |
| 1.25 | 0.042/1.06 | B | 0.043/1.08 | B |
| 1.50 | 0.052/1.31 | B | 0.052/1.33 | B |
| 1.75 | 0.061/1.56 | B | 0.062/1.58 | B |
| 2.00 | 0.071/1.81 | B | 0.072/1.83 | B |
| 2.25 | 0.081/2.06 | B | 0.082/2.08 | B |
| 2.50 | 0.091/2.31 | B | 0.092/2.33 | C |
| 2.75 | 0.101/2.56 | B | 0.102/2.58 | C |
| 3.00 | 0.111/2.81 | C | 0.111/2.83 | C |

Example 13

Figure 16:
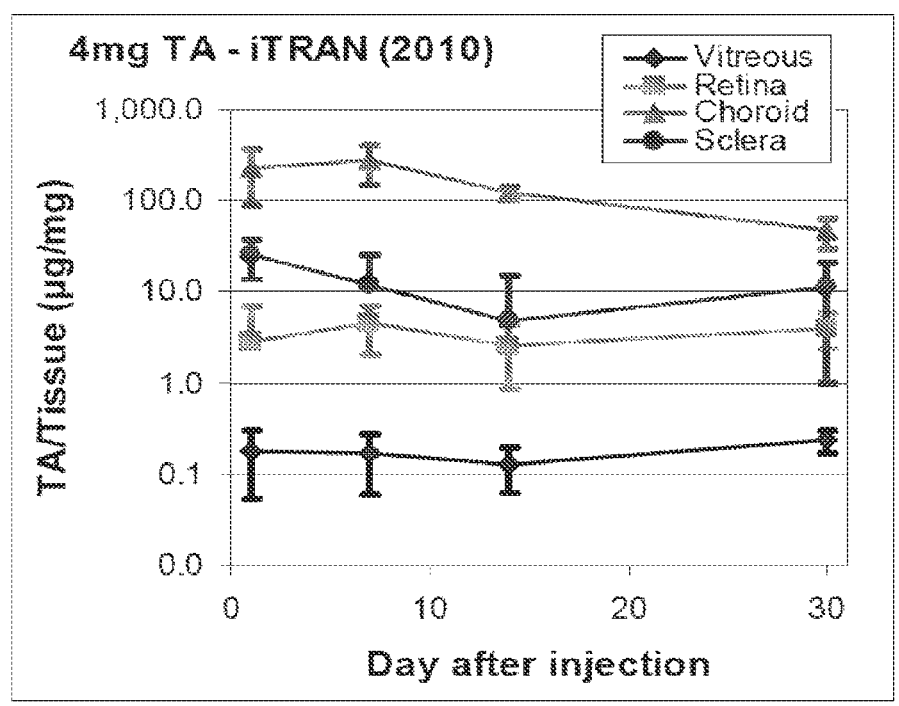
FIG. 16 is a graph of the results of the test described in Example 13.

The device of Example 5 was filled with 0.3 ml of air to act as a fluidic guard. The device was used to access the suprachoroidal space of eyes in anesthetized pigs at the pars plana region of the eye. Once the gas was injected into the suprachoroidal space, the device was used to inject 0.1 ml (4 mg) of triamcinolone acetonide suspension (Kenalog-40, Bristol Meyers Squib). Twelve eyes were injected and three each harvested at 1, 7, 14 and 30 days post injection. The eyes were dissected and 6 mm punches taken from the vitreous, retina, choroid and sclera at four quadrants of the eye and also the posterior retina. The level of drug in the tissues was assayed by solvent extraction of the tissues and quantitation by reverse phase HPLC. The results shown in FIG. 16 demonstrated sustained availability of triamcinolone acetonide in all regions of the eye, including the posterior retina through 30 days with the highest level of drug in the choroid and decreasing levels of drug in the sclera, retina and vitreous.

What is claimed is:

1. A method of administering a therapeutic substance to a target region of an eye, the method comprising:
   inserting a distal end portion of a puncture member into a first portion of the eye, with the distal end portion of the puncture member disposed within the first portion, advancing, automatically in response to reduced resistance provided by the target region, an elongate member relative to the first portion of the eye to displace a second portion of the eye relative to the first portion to at least one of create or expand the target region; the target region being disposed between the first portion and the second portion, and the elongate member having a solid shape including a distal end configured to fit slidably within the puncture member;

with the target region created or expanded, withdrawing the elongate member relative to the first portion of the eye; and conveying, through a lumen of the puncture member, the therapeutic substance into the target region.

2. The method of claim 1, wherein the conveying occurs after the withdrawing is initiated.

3. The method of claim 1, further comprising:
contacting an outer surface of the eye with a stopper associated with the puncture member to control a depth of entry of the puncture member during the inserting.

4. The method of claim 1, wherein the inserting includes inserting the distal end portion of the puncture member tangentially relative to a natural curvature of the eye.

5. The method of claim 1, wherein the elongate member is a wire.

6. The method of claim 5, wherein the distal end of the wire is rounded.

7. The method of claim 1, wherein the puncture member is a hollow needle.

8. The method of claim 1, further comprising viewing, via an imaging system that is external to the eye, the elongate member extending beyond a terminal end of the puncture member and being in contact with the second portion, and the distal end portion of the puncture member within the target region.

9. The method of claim 1, wherein the puncture member is associated with a syringe configured to convey the therapeutic substance through the lumen of the puncture member.

10. The method of claim 1, wherein the elongate member has a blunt tip.

11. The method of claim 1, wherein the first portion is a sclera of the eye, the second portion is a choroid of the eye, and the target region is a suprachoroidal space of the eye.

12. The method of claim 1, wherein the target region is a subretinal space of the eye.

13. The method of claim 1, wherein the advancing the elongate member includes advancing the elongate member through the lumen of the puncture member to displace the second portion of the eye.

14. The method of claim 1, further comprising, prior to the inserting, dissecting an outer portion of the eye.

15. The method of claim 1, wherein the first portion is a sclera of the eye, the second portion is a choroid of the eye, and the target region is a suprachoroidal space of the eye (SCS), the advancing the elongate member includes advancing the elongate member through the lumen of the puncture member to displace the choroid of the eye relative to the sclera to at least one of create or expand the SCS.

16. The method of claim 15, wherein the elongate member has a blunt tip, and further comprising: viewing, via an imaging system that is external to the eye, the elongate member extending beyond a terminal end of the puncture member and being in contact with the choroid, and the distal end portion of the puncture member within the SCS.

17. The method of claim 1, wherein the elongate member is operably coupled to an energy storage member, and the advancing includes the energy storage member exerting a force on the elongate member that is insufficient to advance the elongate member when the distal end of the elongate member is in the first portion but sufficient to advance the elongate member when the distal end of the elongate member is in the target region.

18. The method of claim 1, wherein the elongate member is operably coupled to a spring, and the advancing includes the spring exerting a force on the elongate member that is insufficient to advance the elongate member when the distal end of the elongate member is in the first portion but sufficient to advance the elongate member when the distal end of the elongate member is in the target region.

19. The method of claim 1, wherein the elongate member is substantially linear.

20. The method of claim 1, wherein the elongate member has a substantially constant cross-sectional area.

21. A method of administering a therapeutic substance to a target region of an eye, the method comprising:
inserting a distal end portion of a puncture member into a first portion of the eye;

with the distal end portion of the puncture member disposed in the first portion of the eye, advancing an elongate member relative to the first portion of the eye to displace a second portion of the eye relative to the first portion to at least one of create or expand the target region; the elongate member being solid and having a distal end, the distal end of the elongate member configured to fit slidably within the puncture member, and the target region being disposed between the first portion and the second portion;

with the target region created or expanded, withdrawing the elongate member relative to the first portion of the eye; and conveying the therapeutic substance into the target region.

22. The method of claim 21, wherein the conveying includes conveying the therapeutic substance through a lumen defined by the puncture member.

23. The method of claim 22, wherein the elongate member is flexible.

24. The method of claim 22, wherein the first portion is a sclera of the eye, the second portion is a choroid of the eye, and the target region is a suprachoroidal space of the eye.

25. The method of claim 22, wherein the advancing the elongate member includes advancing the elongate member through a lumen of the puncture member to displace the second portion of the eye.

26. The method of claim 21, wherein the elongate member is slidably disposed within a lumen defined by the puncture member.

27. The method of claim 21, further comprising:
contacting an outer surface of the eye with a stopper associated with the puncture member to control a depth of entry of the puncture member during the inserting.

28. The method of claim 21, wherein the inserting includes inserting the distal end portion of the puncture member tangentially relative to a natural curvature of the eye.

29. The method of claim 21, wherein the elongate member has an atraumatic distal end.

30. A method of administering a therapeutic substance to a target region of an eye, the method comprising:
inserting a distal end portion of a puncture member through a first portion of the eye and towards the target region;

as the distal end portion of the puncture member reaches the target region, advancing, with a force provided by a compressive element, an elongate member distally relative to and through a lumen defined by the puncture member to displace a second portion of the eye relative to the first portion to at least one of create or expand the target region; the target region being disposed between the first portion and the second portion, and the elongate member being solid and configured to slidably fit fully within the lumen; and with the target region created or expanded, completely removing the elongate member from the first portion of the eye; and conveying the therapeutic substance into the target region.

31. The method of claim 30, wherein the inserting includes inserting the distal end portion of the puncture member tangentially relative to a natural curvature of the eye.

32. The method of claim 30, wherein the elongate member has an atraumatic distal end.

33. The method of claim 30, wherein the elongate member is flexible.

34. The method of claim 30, wherein the first portion is a sclera of the eye, the second portion is a choroid of the eye, and the target region is a suprachoroidal space of the eye.

35. The method of claim 30, wherein the conveying includes conveying the therapeutic substance through the lumen of the puncture member.

* * * * *